US005385842A

United States Patent [19]
Weimer et al.

[11] Patent Number: 5,385,842
[45] Date of Patent: Jan. 31, 1995

[54] ANTHRAQUINONES AS INHIBITORS OF SULFIDE PRODUCTION FROM SULFATE-REDUCING BACTERIA

[75] Inventors: Paul J. Weimer, Madison, Wis.; James M. Odom, Avondale, Pa.; Frederick B. Cooling, III; Albert G. Anderson, both of Wilmington, Del.

[73] Assignee: E. I. du Pont de Nemours and Company, Wilmington, Del.

[21] Appl. No.: 107,439

[22] Filed: Aug. 13, 1993

Related U.S. Application Data

[63] Continuation-in-part of Ser. No. 652,406, Feb. 7, 1991, abandoned, which is a continuation-in-part of Ser. No. 510,763, Apr. 18, 1990, abandoned.

[51] Int. Cl.$^6$ .................... B09B 3/00; C12N 1/00; A61L 9/01; C10G 32/00
[52] U.S. Cl. .................... 435/262; 435/243; 435/266; 435/281; 208/47
[58] Field of Search .............. 435/184, 262, 32, 262.5, 435/281, 800, 243, 266; 210/601, 764; 208/47

[56] References Cited

U.S. PATENT DOCUMENTS 4,879,240 11/1989 Subtette .................... 435/252.1
4,999,286 3/1991 Gawal et al. .................... 435/7.32

FOREIGN PATENT DOCUMENTS 1249199 10/1989 Japan .
614466 11/1979 Switzerland .

OTHER PUBLICATIONS

Anderson et al. Chemical Abstracts CA116(15):148128g.
Widdel, Anaerobic Bacteria in Habitats Other Than Man, *Barnes and Meads, Eds., Blackwell Scientific Publications*, 157–184, (1987).
Stetler et al., *Science*, vol. 236, pp. 822–825, (1987).
Odom et al., *Ann. Rev. Microbio.*, vol. 38, 551–592, (1984).
Peck et al., Trends in the Biology of Fermentations For Fuels and Chemicals, *Plenum Publishing*, (1981) pp. 375–395.
Panknania et al., *J. Gen. Microbiol.*, vol. 132, pp. 3357–3365, (1986).
Ringas et al., *Corrosion Engineering*, vol. 44(6), pp. 386–396, (1987).
Davies et al., *Brit. J. Pharmacol.*, vol. 9, pp. 192, (1954).
Wilson et al., *J. Biol. Chem.*, vol. 233, pp. 975–981, (1958).
Taylor et al., *Current Microbiol.*, vol. 3, pp. 101–103, (1979).
Postgate et al., *J. Gen. Microbio.*, vol. 6, pp. 128–142, (1952).
Saleh et al., *J. Appl. Bact.*, vol. 27(2), pp. 281–293, (1964).
Patel et al., *Indian J. Pharmacol.*, vol. 19, pp. 70–73, (1957).
Anchel, *J. Biol. Chem.*, vol. 177, pp. 169–177, (1949).
Kavanagh, *J. Bacteriol.*, vol. 54, pp. 761–767, (1947).
Anke et al., *Arch. Microbiol.*, vol. 126, pp. 223–230, (1980).
Anke et al., *Arch. Microbiol.*, vol. 126, pp. 231–236, (1980).
Bakola–Christianopoulou et al., *Eur. J. Med. Chem.*, vol. 21(5), pp. 385–399, (1986).
Haran et al., *Isr. J. Med. Sci.*, vol. 17(6), PP. 485–496, (1981).
Boos et al., *FEBS Lett.*, vol. 127, pp. 40–44, (1981).
Shcherbanovski et al., *Rastit. Resur.*, vol. 11(3), pp. 445–454 (1975).
Jameel, *Journal WPCF*, vol. 61(2), pp. 230 (1988).
Dezham et al., *Journal WPCF*, vol. 60(4), p. 514 (1988).
Rogers, *Soc. of Chem. Ind.*, pp. 34–39, (Feb. 1940).
Rogers, *Soc. of Chem. Ind.*, vol. 64, pp. 292–295, (Oct. 1945).
Weimer et al., *Appld. and Environmental Microbiology*, pp. 386–396, (Feb. 1988).
Haran et al., *Isr. J. Med. Sci.*, vol. 17, pp. 485–496, (1981).

*Primary Examiner*—Michael G. Wityshyn
*Assistant Examiner*—Timothy J. Reardon

[57] ABSTRACT

A process for inhibiting sulfide production by sulfate-reducing bacteria by contacting certain anthraquinones with the medium containing the sulfate-reducing bacteria is disclosed, as well as an automated screening test for such inhibition.

25 Claims, 2 Drawing Sheets

ANTHRAQUINONES AS INHIBITORS OF SULFIDE PRODUCTION FROM SULFATE-REDUCING BACTERIA

This application is a continuation-in-part of U.S. patent application Ser. No. 07/652,406, filed Feb. 7, 1991, now abandoned, which is a continuation-in-part of U.S. patent application Ser. No. 07/510,763, filed Apr. 18, 1990, now abandoned.

FIELD OF THE INVENTION

The first aspect of the invention is the novel discovery that many anthraquinones, or the corresponding anthraquinol or tetrahydroanthraquinone derivatives thereof, inhibit sulfide production from sulfate-reducing bacteria and are thus potentially useful chemicals for treating industrial situations where biological sulfide generation is a problem. Examples include the prevention of souring of oil wells with hydrogen sulfide or the contamination of surface operations such as pipelines, and storage tanks with hydrogen sulfide. The second aspect is the relative specificity of the anthraquinones, anthraquinols or tetrahydroanthraquinones for the process of respiratory sulfate reduction. This aspect extends the useful application of these inhibitors to situations where only sulfate-reducers should be inhibited, but not other bacterial types, as for example, in sewage treatment where bacterial digestion is desirable but sulfide generation is not, or in the utilization of biomass for the generation of fuel gases where hydrogen sulfide is a deleterious contaminant, or in the agricultural sphere where sulfide generation and consequent soil alkalinity may be a problem for rice cultivation.

Hereinafter, the term "anthraquinone(s)" as used in this application is defined to include anthraquinone compounds, the corresponding anthraquinol derivatives, the corresponding tetrahydroanthraquinone compounds, the corresponding octahydroanthraquinone compounds, and the reduced derivatives thereof.

It is proposed that the anthraquinones are a novel treatment for the problem of hydrogen sulfide pollution by virtue of their relatively benign environmental impact, which is due to their relatively specific toxicity for respiratory sulfide generation. As a consequence, these compounds may be useful in treating situations that are incompatible with the use of broad-spectrum biocides.

BACKGROUND OF THE INVENTION

A recent review by Widdel (1986) in Anaerobic Bacteria in Habitats Other Than Man, pp 157-184, Eds. Barnes and Mead, Blackwell Scientific Publications, includes as sulfate-reducing bacteria the genera: Desulfovibrio, Desulfotomaculum, Desulfobacter, Desulfobulbus, Desulfococcus, Desulfonema, Desulfosarcina and Thermodesulfobacterium. Significant inter- and even intra-generic differences exist in terms of morphologies, ecological niches, and metabolic capabilities. However, all respiratory sulfate-reducing bacteria are strict anaerobes which are poisoned by oxygen. The preponderance of isolates are eubacterial and classified as Desulfovibrio although extremely thermophilic archaebacterial sulfate-reducers have been isolated from undersea volcanoes (Stetter et al., 1987 Science 236:822-825). Thus, the term sulfate-reducer encompasses a broad spectrum of organisms across both eubacterial and archaebacterial branches of bacterial phylogeny.

The metabolic capabilities of the genus Desulfovibrio reflect the range of available niches. Utilization of sulfate as an electron sink and respiratory substrate is the characteristic and predominant mode of energy generation. However, nitrate, elemental sulfur, fumarate and other sulfur oxy-acids, when present, can also serve in a similar capacity for a few species. These bacteria are specialists adapted to use the metabolic end-products of primary degradative bacteria for electron and carbon sources as described by Odom et al., 1981 in Trends in the Biology of Fermentations for Fuels and Chemicals, Eds. Hollaender, Rabson, Rogers, Pietro, Valentine, and Wolfe, Plenum Publishing and Odom et al., 1984 Ann. Rev. Microbiol. 38:551–592. Organic acids such as lactate, formate, and pyruvate, alcohols such as ethanol, and molecular hydrogen are the preferred electron sources for sulfate reduction. Acetate, which is the metabolic end-product of the Desulfovibrio, can be utilized by Desulfobacter as an electron donor with carbon dioxide as the sole end product (Stetter et al., 1987 Science 236:822-825). Thus, the sulfate-reducers can effect total mineralization of organic matter from the level of alcohols and acids to carbon dioxide.

The sulfate-reducers play a special role in methane formation as it occurs in sewage treatment and freshwater bogs. In these situations, where sulfate concentrations are very low, the sulfate-reducer enters into a symbiotic relationship with methane-producing bacteria (methanogen) wherein the sulfate-reducers actually produce hydrogen from organic acids and alcohols only if the hydrogen is continuously consumed by the methanogen. This important process, termed interspecies hydrogen transfer, is a vital link in the food chain from complex polymers to methane (Odom et al., 1981 in Trends in the Biology of Fermentations for Fuels and Chemicals, Eds. Hollaender, Rabson, Rogers, Pietro, Valentine, and Wolfe, Plenum Publishing). The most intensively studied aspect has been hydrogen metabolism due to its inherent relationship with methane (fuel) generation from biomass. Similarly, the implication of microbial hydrogen uptake in the phenomenon of anaerobic corrosion of steel according to the theory of cathodic depolarization has stimulated research into the the hydrogen metabolism of sulfate-reducers as well as other microbial types (Von Wolzogen Kuhr et al., 1934 Water 18:147-165, Odom et al., 1984 Ann. Rev. Microbiol. 38:551-592, Pankhania et al., 1986 J. Gen. Microbiol. 132:3357-3365, and Ringas et al., 1987 Corrosion Engineering 44 #6:386-396).

There are currently approximately 130 different industrial biocide products registered with the U.S. Environmental Protection Agency which are produced by over a 100 different companies in the U.S. alone. The leading biocides are halogenated compounds, which make up 35% of total sales, while quarternary detergents and phenolics represent 22% of total sales. Organometallic compounds, inorganic compounds, aldehydes, anilides, and organosulfur compounds make up the rest of the total. None of the known commercial chemicals are specific for sulfate-reducing bacteria, but many have demonstrated effectiveness against sulfate-reducers. Below are discussed some of the more commonly used inhibitors against sulfate-reducing bacteria.

Organo-sulfur or sulfur-nitrogen compounds contain some of the more effective industrial biocides against sulfate-reducers. The isothiazoline containing compounds (produced by Rohm & Haas, Inc. under the name "Kathon®") are effective against, but not specific for, sulfate-reducers at 12-ppm (Oil and Gas Journal Mar. 8, 1982, p 253). The thiocyanate containing compounds are effective in the range of 5–30 ppm (i.e. "Cytox®"). 2,2-Dibromo-3-nitrilopropionamide (DBNPA) is produced by Nalco, Inc. and is claimed to be particularly effective against sulfate-reducing bacteria at 3–12 ppm. This compound is also a good surfactant and corrosion inhibitor. Recently, Nalco, Inc. has introduced an oilfield biocide claimed to be effective against sulfate-reducers. The product is essentially metronidazole, which is a pharmaceutical originally used to treat Trichosomal infections. The compound is not specific for sulfate-reducers but is claimed to be generally effective against anaerobic bacteria.

Acids and aldehydes are also effective inhibitors of sulfate-reducers. Glutaraldehyde is widely used in water flooding situations at concentrations in the range of 100 to 2000 ppm. The sole U.S. producer is Union Carbide, Inc. with its own registered "Ucarcide®" formulation. Ucarcide® is claimed to protect oil fields from aerobic and anaerobic microorganisms including sulfate-reducing bacteria in water flooding situations, injection water, drilling and packer fluid. Formaldehyde, which is substantially cheaper, is also used in similar concentrations. These two compounds together comprise the major biocides used in the oil field. Acrolein, an extremely toxic compound, is also effective against sulfate-reducers and is reccommended for use at concentrations in the range of 1 to 15 ppm.

Quarternary amines are a diverse group of compounds containing a quarternary nitrogen atom with long chain alkyl or aromatic substituents. In the oil field these compounds may act as both corrosion inhibitors and bacteriostatic agents. The compounds are used in this application in the 5–100 ppm range. At low concentrations these compounds may be bacteriostatic rather than bacteriocidal. The quarternary amines are generally less hazardous than many oil field biocides, but they must often be used in conjunction with more toxic biocides to enhance their effectiveness.

Halogenated compounds, such as chlorhexidine (a biguanide), (Hibitane® from ICI, Inc.) is a widely used, commercial, antimicrobial compound, and is known to be effective against a number of sulfate-reducing bacteria at concentrations of 1–10 ppm (Davies et al., 1954 Brit. J. Pharmacol. 9:192). This compound or its derivatives are generally effective against most bacterial types and are, therefore, nonspecific. Biguanides such as chlorhexidine appear to function by disruption of the cell membrane which causes release of cytoplasmic contents. There is no available data on any industrial use of this chemical to treat sulfate-reducing bacteria.

Inorganic compounds, such as liquid chlorine, hypochlorites, chlorine dioxide and chloroisocyanurates are strong oxidizing agents, are often found as the active constituents in bleach, and have shown effectiveness in oil field situations against sulfate-reducing bacteria.

Classical inhibitors of sulfate reduction such as molybdate, selenate, and fluorophosphate anions are analogues of sulfate and have been shown to interfere with the primary enzymatic step in the activation of sulfate, i.e., the adenosine 5'-triphosphate (ATP) sulfurylase reaction. Here an unstable phospho-analogue anhydride is formed in place of the phospho-sulfate bond. The consequence of this is that the bacterium eventually depletes its energy reserve of ATP via reaction with these analogues and death ensues (Taylor et al., 1979 Current Microbiol. 3:101–103 and Wilson et al., 1958 J. Biol. Chem. 233:975–981). Sulfate analogues have been used to inhibit sulfate-reduction at concentrations from 5–20 mM (i.e., 1000–4000 ppm molybdate). These levels are impractical from an applications standpoint but the compounds have found use as research tools (Postgate, 1952 J. Gen. Microbiol. 6:128–142 and Saleh et al., 1964 J. Appl. Bact. 27#2:281–293). Furthermore, the sulfate analogues inhibit sulfate assimilation as it occurs in all bacteria and plants, as well as sulfate respiration, and, thus, are not truly specific for sulfate-reducing bacteria.

Antibacterial activity associated with anthraquinones was first discovered in plant extracts of the genus Cassia. (Patel et al., 1957 Indian J. Pharmacol. 19:70–73). Subsequent investigations revealed that the active component of leaf extracts of Cassia sp. was Rhein or 4,5-dihydroxyanthraquinone-2-carboxylic acid (Anchel, 1949 J. Biol. Chem. 177: 169–177). Subsequently, it has become apparent that many anthraquinones have antibacterial properties, however, it is equally clear that these compounds do not inhibit all bacterial types. In one study by F. Kavanaugh it would appear that gram positive organisms such as Bacillus sp. or Staphylococcus are sensitive to anthraquinones while gram negative species such as $E.$ $coli$ or Pseudomonas sp. are rather insensitive (Kavanaugh 1947 J. Bacteriol. 54:761–767). However, even among the gram positive bacteria, antibacterial effects are sporadic and unpredictable. For example, another study showed that 1,4,6,8-tetrahydroxyanthraquinone inhibited 4 species of Bacillus, one strain of Nocardia, one strain (out of four tested) of Streptomyces and one of the Gram negative Proteus. The compound did not affect any species of $E.$ $coli,$ Pseudomonas, Salmonella or Sarcina (Anke et al., 1980 Arch. Microbiol. 126:223–230 and Anke et al., 1980 Arch Microbiol., 126:231–236). A study by Bakola-Christianopoulou et al. 1986 Eur. J. Med. Chem.-Chim. Ther. 21#5:385–390, where the metal chelates of the anthraquinones were studied, showed that 1,8-dihydroxyanthraquinone was inactive against $B.$ $aureus,$ $B.$ $subtilis,$ $B.$ $stearothermophilus$ and $S.$ $aureus.$ In the same study 1,2-dihydroxyanthraquinone and 1-amino-4-hydroxyanthraquinone were either inactive against these strains or required concentrations in excess of 100 to 1000 ppm for inhibition. These workers also concluded that the metal chelates were more active than the free uncomplexed compounds and that the compounds showed the most activity against the gram positive Bacillus sp. These results are typical of the published studies on the antibacterial activity of anthraquinones.

Swiss Patent No. 614,466 of Mycogel Laboratories Inc., Brooklyn, N.Y., entitled Agent for Inhibiting the Growth of Bacteria in Culture Media and Use of the Agent describes the use of compounds derived from paraquinone or their hemiquinone or glycoside derivatives as agents for use in culture media for cultivating fungi and yeasts. The rationale disclosed was that these compounds inhibit bacterial growth but not the growth of eukaryotic cells such as molds and yeasts. Preferred anthraquinone derivatives claimed include those substituted with methyl, hydroxymethyl, carboxyl, aldehyde and carboxyethyl groups. Haran et al., 1981 Isr. J. Med. Sci. 17#6:485–496, demonstrated that certain diaminoanthraquinone derivatives exhibited toxicity against gram positive cocci and that gram negative bacteria were rather insensitive.

The mode of action of anthraquinones on bacterial metabolism is not clear and may be multitudinous. It is clear that the inhibitory effect is only observed with bacteria and not with plant, fungal or mammalian tissue, hence, the compounds are relatively non toxic to higher life forms. It is known that many anthraquinones interfere with bacterial DNA metabolism, presumably at the site of DNA directed RNA polymerase (Anke et al., 1980 Arch Microbiol., 126:231-236). Anthraquinone-containing compounds have also been shown to inhibit mitochondrial ADP transport (Boos et al., 1981 FEBS Lett. 127:40-44). It is also known that reduced anthraquinones may react chemically with oxygen to produce the highly toxic superoxide radical and this is generally very toxic to bacteria (Shcherbanovskii et al., 1975 Rastit. Resur. 11#3:445-454).

The consensus from the existing literature is that anthraquinones are not generally antimicrobial. The organisms that are sensitive to anthraquinones have been Gram positive bacteria, in particular Bacillus sp. The anthraquinones do exhibit an array of unrelated and unpredicted biological effects as briefly listed above. The inhibition of sulfide production by anthraquinones is unreported in the literature and appears to be another example of an unpredicted and unrelated biological effect, particularly considering that the sulfate-reducers are Gram negative organisms.

It is clear that sulfide pollution is a growing industrial and environmental concern for which there exists no truly effective or adequate treatment that is environmentally sound. The chemical treatments that are available have a number of shortcomings. Many of these chemicals are highly reactive with short effective lives as antimicrobials and therefore high concentrations are required. Secondly, due to their inherent toxicity, these compounds may pose a health hazard to the personnel using them. Thus a need exists for better means of controlling sulfide pollution.

One key and important difference between existing chemicals and the compounds of the instant invention is the relatively unreactive nature of a number of anthraquinones as a group. In fact, 1,8-dihydroxyanthraquinone (one of our most potent compounds) has been sold commercially as a laxative (see Physicians' Desk Reference, page 574 for Modane ®, and page 575 for Modane Plus ®). Many anthraquinones, including derivatives of 1,8-dihydroxyanthraquinone, are naturally-occurring in a number of plants such as rhubarb (*Rheum officinale*). Use of plant extracts include senna in Senakot ® Tablet and Senokot-S ® (see Physician's Desk Reference, pages 1596-1597), and casenthranol in Dialose Plus ® (see Physicians' Desk Reference, page 1979).

The specific inhibitory activity of the compounds of the present invention and their lack of toxicity to many other organisms opens up entirely new possibilities for use in various waste treatment situations where conventional biocides cannot be used. For example, the odor associated with sulfide pollution in sewage treatment is both a health hazard and an aesthetic problem for many communities. More significantly, from the economic standpoint, concrete conduits are damaged from the aerobic oxidation of sulfide to sulfuric acid. This is a particular problem for cities such as Miami or Los Angeles where the distances involved in sewage transit at ambient temperatures mean long residence times, high metabolic activity and tremendous destruction of concrete structures. The current "state of the art" method to treat this problem is to precipitate the sulfide from solution using massive amounts of ferrous chloride. This alleviates the odor problem but does not remove the sulfide as a substrate for acid producing bacteria (Jameel 1988 Journal WPCF 61#2:230 and Dezham et al., Journal WPCF 60#4:514). The instant invention is particularly advantageous for this kind of application.

SUMMARY OF THE INVENTION

The present invention relates to a process for inhibiting sulfide production by sulfate-reducing bacteria comprising contacting certain anthraquinone compounds with the medium containing the sulfate-reducing bacteria.

The present invention further comprises an automated process for the testing of compounds for inhibition of sulfide production by bacteria.

DETAILED DESCRIPTION OF THE INVENTION

Figure 1:
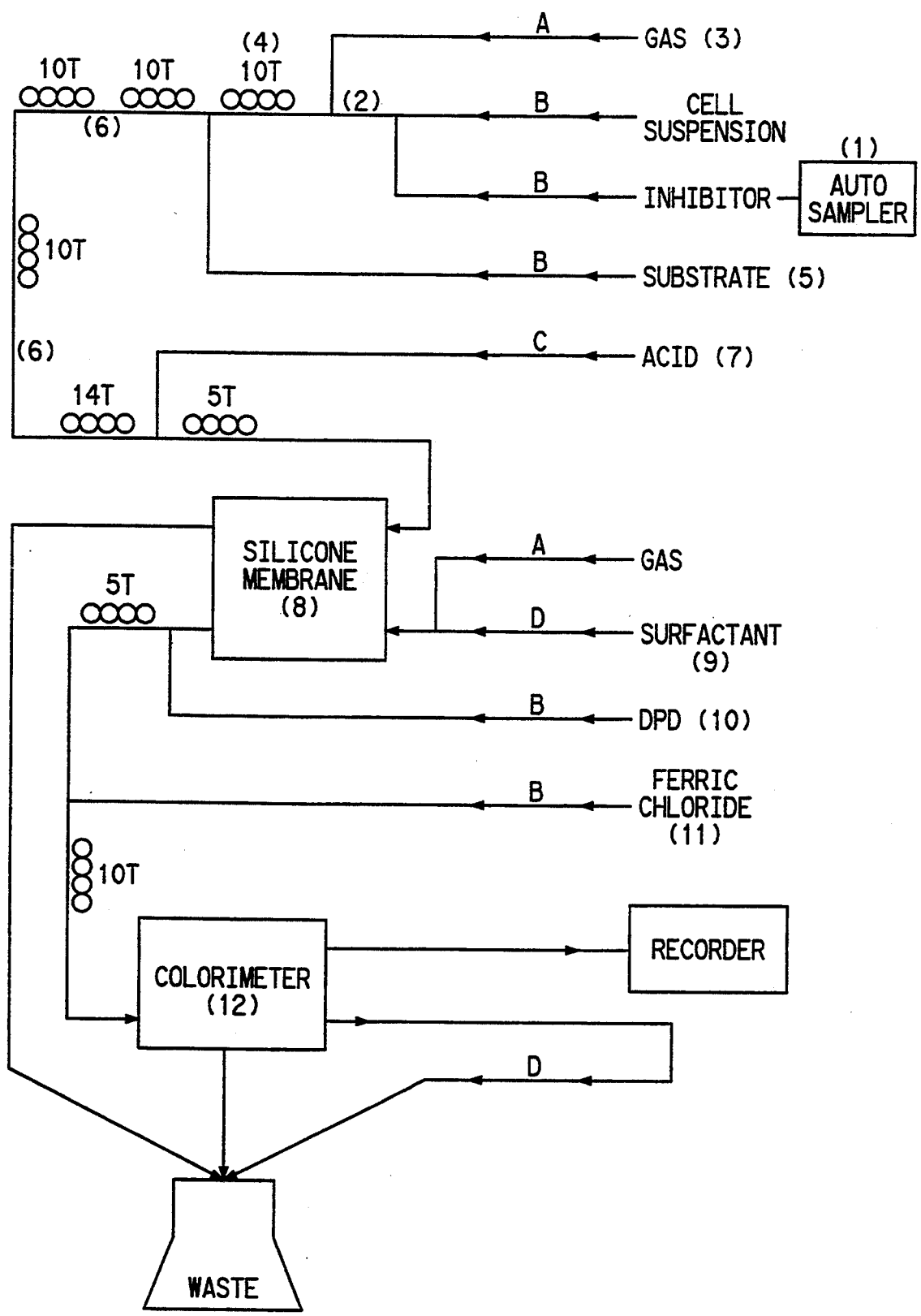
FIG. 1 is a schematic of an automated analyzer used to screen anthraquinones for inhibition of sulfide production.

This invention comprises a process to inhibit sulfide production by sulfate-reducing bacteria comprising contacting or dispersing certain anthraquinones with the medium which contain the sulfate-reducing bacteria. The term "anthraquinone(s)" as used herein is as previously defined under Field of the Invent ion.

Many anthraquinones are commercially available. The preparation of anthraquinol derivatives from anthraquinones is known to those skilled in the art. For example, 1,8-dihydroxy-9-anthranol can be prepared by reduction of 1,8-dihydroxyanthraquinone using hydrogen and a nickel catalyst, K. Zahn and H. Koch, *Chemische Berichte*, 17B, 172 (1938) or by use of phosphorous and hydriodic acid. 1,2,10-Anthracenetriol can be prepared by reduction of 1,2-dihydroxyanthraquinone using ammonium hydroxide and zinc, H. Roeruer, *Chemische Berichte*, 14, 1259 (1881), C. Grabe and C. Thode, *Liebig's Annalen der Chemic*, 349, 207 (1906). These and similar reductions are summarized in *Das Anthracen und die Anthrachinone*, H. Houben, Georg Thieme pub., 1929, Leipzig, pp. 193-195. Reduction methods for preparation of hydroanthraquinones are found in *Das Anthracen und die Anthrachinone*, H. Houben, Georg Thieme, pub., 1929, Leipzig, pp 183-186. For example, the preparation of tetrahydroanthraquinones, and various reduced derivatives are described in U.S. Pat. No. 1,967,862 issued Jul. 24, 1934 and U.S. Pat. No. 4,642,393 issued Feb. 10, 1987; Diels and Alder, Ber., 62, 2337 (1929); Carothers et al., J. Amer. Chem. Soc., 54, 4071 (1932); and Euler et al., Ber., 53B, 822 (1920).

The activity of various anthraquinones in the inhibition of sulfide production by sulfate-reducing bacteria can be predicted based upon analysis of the substituents present. A total of 147 different active anthraquinones were named according to the rules found in the 7th Collective Index of Chemical Abstracts. Following this convention, a multiple linear regression analysis of the activity data resulted in the creation of formula (I)

$$\text{Activity} = 28.1 + \Sigma(\text{coeff.}) \qquad (I)$$

wherein activity refers to the percent reduction of $H_2S$ production, 28.1 is a constant, and $\Sigma$ (coeff.) refers to the sum of the coefficient values. Coefficient values are given in the coefficients table, Table C, for each individual substituent $R_1$ through $R_8$ present in the anthraquinones represented by structure (A), or the corresponding derivatives thereof.

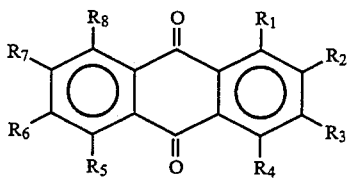

(A)

As an example, the activity of the anthraquinone substituted as shown below is predicted to be 26.4 from the formula. The observed value is 26.0.

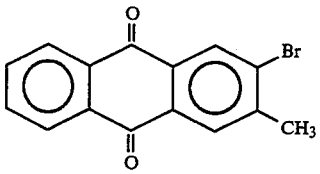

Anthraquinones having substituents with positive values in the coefficient table increase activity while those that have substituents with negative values decrease activity. Anthraquinones having substituents whose coefficients yield positive activity in formula (I) are active and those with an activity above at least 21 in the formula are most active and preferred. Those having substituents whose coefficients yield a negative activity in formula (I) are not active. The compounds may possess some substituents having negative coefficients and still retain overall activity. These negative substituents can serve other purposes, such as increasing solubility.

It should be noted that the standard deviation of regression for the formula is 20.7; therefore, the values calculated from the formula are $+20.7$.

Especially suitable for use herein are anthraquinones of structure A wherein $R_1$ is alkyl, aryl, amino, $NO_2$, NO, diazonium, amido, sulfonamido, arylamino, hydroxy, alkoxy, alkyl ether, aryl ether, sulfo, chloro, or bromo;

$R_2$ is alkyl, aryl, carboxy, amino, $NO_2$, NO, diazonium, amido, sulfonamide, arylamino, hydroxy, alkoxy, alkyl ether, aryl ether, sulfo, chloro, or bromo;

$R_3$ is alkyl, aryl, carboxy, hydroxy, alkoxy, alkyl ether, aryl ether, sulfo, or chloro;

$R_4$ is alkyl, aryl, amino, $NO_2$, NO, diazonium, amido, sulfonamido, arylamino, hydroxy, alkoxy, alkyl ether, aryl ether, chloro, or bromo;

$R_5$ is amino, $NO_2$, NO, diazonium, amido, sulfonamido, arylamino, hydroxy, alkoxy, alkyl ether, aryl ether, sulfo, chloro, or bromo;

$R_6$ is alkyl, aryl, amino, $NO_2$, NO, diazonium, amido, sulfonamido, arylamino, hydroxy, alkoxy, alkyl ether, aryl ether, sulfo, or chloro;

$R_7$ is alkyl, aryl, hydroxy, or sulfo; and $R_8$ is hydroxy or chloro.

TABLE A

| Substituent Name and Ring Position | Coefficient | Substituent Name and Ring Position | Coefficient |
|---|---|---|---|
| 1 C1 | 5.3 | 28 OH5 | −5.6 |
| 2 C2 | 7.0 | 29 OH6 | −7.8 |
| 3 C3 | −9.2 | 30 OH7 | −1.5 |
| 4 C4 | −16.3 | 31 OH8 | 4.7 |
| 5 C6 | −6.9 | 32 OR1 | −23.1 |
| 6 C7 | −42.6 | 33 OR2 | −7.4 |
| 7 Carb2 | 35.0 | 34 OR3 | 3.1 |
| 8 Carb3 | −53.0 | 35 OR4 | 29.1 |
| 9 N1amine, N1NO2, N1NO, N1diazonium | −0.2 | 36 OR5 | 31.0 |
| 10 N1amide | −19.4 | 37 OR6 | 78.4 |
| 11 N1aryl | −5.4 | 38 S1 | −4.8 |
| 12 N2amine N1NO2, N1NO, N1diazonium | −7.0 | 39 S2 | −3.7 |
| 13 N2amide | −7.7 | 40 S3 | 4.8 |
| 14 N2aryl | 1.8 | 41 S5 | −5.2 |
| 15 N4amine N1NO2, N1NO, N1diazonium | −19.6 | 42 S6 | −11.0 |
| 16 N4amide | −24.0 | 43 S7 | −15.4 |
| 17 N4aryl | −14.0 | 44 CL1 | 25.0 |
| 18 N5amine N1NO2, N1NO, N1diazonium | 4.4 | 45 CL2 | 25.8 |
| 19 N5amide | 6.0 | 46 CL3 | −1.9 |
| 20 N5aryl | 8.4 | 47 CL4 | −12.6 |
| 21 N6amine N1NO2, N1NO, N1diazonium | −1.0 | 48 CL5 | 18.9 |
| 22 N6amide | −20.5 | 49 CL6 | −4.9 |
| 23 N6aryl | −4.6 | 50 CL8 | −12.7 |
| 24 OH1 | 12.1 | 51 Br1 | −8.4 |
| 25 OH2 | 6.0 | 52 Br2 | 7.5 |
| 26 OH3 | −13.0 | 53 Br4 | −14.5 |
| 27 OH4 | −9.6 | 54 Br5 | 3.1 |

Number of data points = 147
Standard deviation of regression = 20.7

The abbreviations for the substituents are explained as follows:

"C" refers to any alkyl or aryl group bound to the anthraquinone ring by a covalent carbon-carbon bond.

"Carb" refers to any carboxylic acid group, $CO_2H$, bound to the anthraquinone ring.

"N-amine" refers to any amino group, $NR_1R_2$, where $R_1$ and $R_2$ may be H or alkyl; $NO_2$, diazonium, or NO groups have the same coefficient value since under the reducing conditions present, these are expected to be reduced to amine groups.

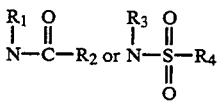

where $R_1$, $R_2$, $R_3$, $R_4$ may be H, alkyl groups or aryl rings.

"N-aryl" refers to aryl amine groups, such as phenylamino, $C_6H_5NR_1R_2$ wherein $R_1$ and $R_2$ are each hydrogen or alkyl. "N-aryl" also refers to N-heterocyclic aromatic ring attached to the anthraquinone ring at a nitrogen atom in the N-heterocyclic group.

"OH" refers to the hydroxyl group.

"OR" refers to alkoxy, or to alkyl or aryl ethers.

"S" refers to $SO_3H$ group.

"CL" and "Br" refer to the chloro and bromo groups.

The number with each substituent refers to the position on the anthraquinone ring to which the substituent is attached.

Anthraquinones or anthraquinone precursors or derivatives suitable for the inhibition of sulfide production by sulfate-producing bacteria in the process of the present invention include the following:

N-[1-(9,10-dihydro-9,10-dioxo)anthracenyl]-N'-(1-methylethyl)imidodicarbonimidic diamide hydrochloride
CA Reg. No.: None
Source: E. I. du Pont de Nemours and Company
1-Aminoanthraquinone (97%)
CA Reg. No.: 82-45-1
Source: Aldrich Chemical Co., Inc.
940 West Saint Paul Avenue
Milwaukee, WI 53233
2-Aminoanthraquinone
CA Reg. No.: 117-79-3
Source: Aldrich
1-Amino-4-Hydroxyanthraquinone
CA Reg. No.: 116-85-8
Source: Kodak Laboratory Chemicals
Building 70
Eastman Kodak Co.
343 State Street
Rochester, NY 14650
1,2-Diaminoanthraquinone
CA Reg. No.: 1758-68-5
Source: Aldrich
2,6-Dihydroxyanthraquinone; Anthraflavic acid
CA Reg. No.: 84-60-6
Source: Aldrich
Anthraquinone-2-carboxylic acid (98%)
CA Reg. No.: 117-78-2
Source: Aldrich
1,5-Dihydroxyanthraquinone; Anthrarufin (92%)
CA Reg. No.: 117-12-4
Source: Pfaltz and Bauer, Inc.
Division of Aceto Chemical Co., Inc.
172 East Aurora Street
Waterbury, CT 06708
1,2-Dihydroxyanthraquinone; Alizarin
CA Reg. No.: 72-48-0
Source: Aldrich
2,2'-[(9,10-Dihydro-9,10-dioxo-1,5-anthracenediyl)diimino]bis[5-methylbenzenesulfonic acid], di Na salt; Alizarine violet 3R
CA Reg. No.: 6408-63-5
Source: Aldrich
1,2,5,8-Tetrahydroxyanthraquinone; Quinalizarin
CA Reg. No.: 81-61-8
Source: Aldrich
4-Amino-9,10-dihydro-1,3-dihydroxy-9,10-dioxo-2-anthracenesulfonic acid, monosodium salt; Nuclear fast red
CA Reg. No.: 6409-77-4
Source: Aldrich
1,8-Dihydroxyanthraquinone; Danthron
CA Reg. No.: 117-10-2
Source: Aldrich
2,2'-[(9,10-Dihydro-9,10-dioxo-1,4-anthracenediyl)diimino]bis[5-methylbenzenesulfonic acid],di Na salt; Acid green 25
CA Reg. No.: 4403-90-1
Source: Aldrich
1-Amino-2,4-bromoanthraquinone
CA Reg. No.: 81-49-2
Source: Pfaltz & Bauer
5-Chloro-1-anthraquinonylamine
CA Reg. No.: 117-11-3
Source: Pfaltz & Bauer
2-Ethylanthraquinone (97+%)
CA Reg. No.: 84-51-5
Source: Aldrich
1-Hydroxyanthraquinone (97%)
CA Reg. No.: 129-43-1
Source: Aldrich
2-(Hydroxymethyl)anthraquinone (97%)
CA Reg. No.: 17241-59-7
Source: Aldrich
1-Amino-4-methoxyanthraquinone
CA Reg. No.: 116-83-6
Source: Aldrich
1-Amino-6,7-dichloroanthraquinone
CA Reg. No.: 5355-88-4
Source: Aldrich
Benz[a]anthracene-7,12-dione (97%)
CA Reg. No.: 2498-66-0
Source: Aldrich
1,8-Dihydroxy-3-methylanthraquinone; Chrysophanic acid
CA Reg. No.: 481-74-3
Source: Aldrich
10-[(3-Amino-2,3,6-trideoxy-alpha-L-lyxo-hexopyranosyl)oxy]-7,8,9,10-tetrahydro-6,8,11-trihydroxy-8-(hydroxyacetyl)-1-methoxy-5,12-naphthacenedione hydrochloride; Adriamycin hydrochloride
CA Reg. No.: 23214-92-8
Source: Aldrich
9,10-Dihydro-4,5-dihydroxy-9,10-dioxo-2-anthracenecarboxylic acid; Rhein
CA Reg. No.: 478-43-3
Source: Aldrich
(8S-cis)-8-Acetyl-10[(3-amino-2,3,6-trideoxy-alpha-L-lyxo-hexopyranosyl)oxy]-7,8,9,10-tetrahydro-6,8,11-trihydroxy-1-methoxy-5,12-naphthacenedione hydrochloride; Daunomycin hydrochloride
CA Reg. No.: 20830-81-3
Source: Sigma Chemical Co., Inc.
P.O. Box 14508
Saint Louis, MO 63178
1,2,4-Trihydroxyanthraquinone; Purpurin
CA Reg. No.: 81-54-9
Source: Aldrich
1-Aminoanthraquinone diazonium salt
CA Reg. No.: 16048-40-1
Source: K&K Laboratories
Division of ICN Biomedicals, Inc.
4911 Commerce Parkway
Cleveland, OH 44128
2,2'-Dimethyl-[1,1'-bianthracene]-9,9',10,10'-tetrone; 2,2'-Dimethyl-1,1'-bianthraquinone
CA Reg. No.: 81-26-5
Source: Aldrich
3-(D-apio-beta-D-Furanosyloxy)-1,8-dihydroxy-6-methyl-9,10-anthracenedione; Frangulin B
CA Reg. No.: 14101-04-3
Source: Pfaltz & Bauer
2-Chloroanthraquinone 99%
CA Reg. No.: 131-09-9
Source: Aldrich
1,5-Dichloroanthraquinone (96%)
CA Reg. No.: 82-46-2
Source: Aldrich
1,4,5,8-Tetrachloroanthraquinone
CA Reg. No.: 81-58-3
Source: K & K
1-Chloroanthraquinone
CA Reg. No.: 82-44-0
Source: Aldrich
1,8-Dichloroanthraquinone (97%)
CA Reg. No.: 82-43-9
Source: Aldrich
2-Bromo-3-methylathraquinone
CA Reg. No.: 84-44-6
Source: Pfaltz & Bauer
2-(2,2,2-Trimethylpropionamido)anthraquinone
CA Reg. No.: None
Source: Aldrich
2,6-Bis[2-(dimethylamino)ethoxy]-9,10-anthracenedione; Tilorone analog R11,043DA
CA Reg. No.: 66686-31-5
Source: Sigma
2-Methyl-1-nitroanthraquinone
CA Reg. No.: 129-15-7
Source: Lancaster Synthesis Ltd.
P.O. Box 1000
Windham, NH 03087
1-Amino-9,10-dihydro-9,10-dioxo-2-anthracenesulfonic acid; 1-Aminoanthraquinone-2-sulfonic acid
CA Reg. No.: 83-62-5
Source: Aldrich
9,10-Dihydro-5-nitro-9,10-dioxo-1-anthracenesulfonic acid; 5-Nitroanthraquinone-1-sulfonic acid
CA Reg. No.: 82-50-8
Source: Aldrich
3-Chloro-9,10-dihydro-9,10-dioxo-2-anthracenecarboxylic acid; 2-Chloroanthraquinone-3-carboxylic acid
CA Reg. No.: 84-32-2
Source: Pfaltz & Bauer -continued Anthraquinone
CA Reg. No.: 84-65-1
Source: Aldrich
1,8-Dihydroxy-3-(hydroxymethyl)-anthraquinone; Aloe-emodin
CA Reg. No.: 481-72-1
Source: Apin Chemicals, Ltd.
Unit 1
Milton Trading Estate
Near Abingdon
Oxon OX14 4RS
United Kingdom
7,16-Dichloro-6,15-dihydro-5,9,14,18-anthrazinetetrone;
7,16-Dichloroindanthrone
CA Reg. No.: 130-20-1
Source: K & K
1,2,3,4,5,8-Hexahydroxyanthraquinone; Alizarin cyanin
CA Reg. No.: None
Source: K & K
2,4,5,7-Tetrabromo-1,8-dihydroxy-9,10-anthracenedione;
2,4,5,7-Tetrabromochrysazin
CA Reg. No.: 17139-66-1
Source: K & K
1,2,7-Trihydroxyanthraquinone; Anthrapurpurin
CA Reg. No.: 602-65-3
Source: Pfaltz & Bauer
1,4,5-Trihydroxy-2-methyl-9,10-anthracenedione;
Islandicin
CA Reg. No.: 476-56-2
Source: Apin
1,4,5,7-Tetrahydroxy-2-methyl-9,10-anthracenedione;
Catenarin
CA Reg. No.: 476-46-0
Source: Apin
1,8-Dihydroxy-3-methoxy-6-methyl-9,10-anthracenedione;
Physcion
CA Reg. No.: 521-61-9
Source: Apin
1,4,5,8-Tetrahydroxy-2-methyl-9,10-anthracenedione;
Cynodontin
CA Reg. No.: 476-43-7
Source: Apin
1,5,8-Trihydroxy-3-methyl-9,10-anthracenedione;
Helminthosporin
CA Reg. No.: 518-80-9
Source: Apin
1-Hydroxy-2-[(6-O-β-D-xylopyranosyl-β-D-glucopyranosyl)-oxy]-9,10-anthracenedione; Ruberythric acid
CA Reg. No.: 152-84-1
Source: Apin
2-Phenoxy quinizarin-3,4'-disulfonic acid, di K salt
CA Reg. No.: None
Source: K & K
(+,−)-1-Acetoxy-8-hydroxy-1,4,4a,9a-tetrahydroanthraquinone
CA Reg. No.: 73794-49-7
Source: Aldrich
1-Amino-4-[[4-[(dimethylamino)methyl]phenyl]amino]-9,10-anthracenedione; Basic Blue 47
CA Reg. No.: 12217-43-5
Source: Aldrich
1,5-Bis(2-carboxyanilino)-9,10-anthracenedione;
Acridylic acid
CA Reg. No.: 81-78-7
Source: Sandoz Chemicals
4000 Monroe Road
Charlotte, NC 28205
1,8-Dihydroxy-9-anthranol; 1,8-Dihydroxyanthranol
CA Reg. No.: 480-22-8
Source: Aldrich
1,2,10-Anthracenetriol; Anthrarobin
CA Reg. No.: 577-33-3
Source: Aldrich
1-Amino-4-bromo-2-methylanthranquinone (99%)
CA Reg. No.: 81-50-5
Source: Aldrich
1,4-Diaminoanthraquinone (97%)
CA Reg. No.: 128-95-0
Source: Aldrich
2,6-Diaminoanthraquinone
CA Reg. No.: 131-14-6

-continued

Source: Aldrich
1-Amino-4[4-[[4-chloro-6[[2, 3 or 4-sulfophenyl]amino]-1,3,5-triazin-2-yl]amino]-3-sulfophenylamino]-9,10-dihydro-9,10-dioxo-2-anthracenesulfonic acid; Reactive blue 2; Procion blue HB(S); Cibacron blue 3G-A; Basilen blue E-3G
CA Reg. No.: 12236-82-7
Source: Aldrich
Anthraquinone-1,5-disulfonic acid, di Na salt hydrate (95%)
CA Reg. No.: 853-35-0
Source: Aldrich
Anthraquinone-2,6-disulfonic acid, di Na salt
CA Reg. No.: 84-50-4
Source: Aldrich
Anthraquinone-2-sulfonic acid, sodium salt monohydrate
CA Reg. No.: 131-08-8
Source: Aldrich
1,2-Bis[(4-sulfophenyl)amino]-4-hydroxyanthraquinone;
Alizarin blue black B
CA Reg. No.: 1324-21-6
Source: Aldrich
3-Aminomethylalizarin-N,N-Diacetic acid
CA Reg. No.: 3952-78-1
Source: Pfaltz & Bauer
1-Amino-4-[[3-(ethenylsulfonyl)phenyl]-9,10-dihydro-9,10-dioxo]-2-anthracene sulfonic acid, monosodium salt;
Acid blue 215
CA Reg. No.: 14541-90-3
Source: Aldrich
1-(Methylamino)anthraquinone (98%)
CA Reg. No.: 82-38-2
Source: Aldrich
2,2'-[(9,10-Dihydro-5,8-dihydroxy-9,10-dioxo-1,4-anthracehdiyl)diimino]bis[5-methylbenzenesulfonic acid], di Na salt; Acid green 41
CA Reg. No.: 4430-16-4
Source: Aldrich
2,2'-[(9,10-Dihydro-9,10-dioxo-1,4-anthracenediyl)-diimino]bis[5-butylbenzenesulfonic acid]; Acid green 27
CA Reg. No.: 6408-57-7
Source: Aldrich
1,1'-Iminobis[4-amino]9,10-anthracenedione, sulfonated;
Acid black 48
CA Reg. No.: 1328-24-1
Source: Aldrich
1-Amino-9,10-dihydro-9,10-dioxo-4-(phenylamino)-2-anthracenesulfonic acid, Na salt; Acid blue 25
CA Reg. No.: 6408-78-2
Source: Aldrich
4-[[4-(Acetylamino)phenyl]amino]-1-amino-9,10-dihydro-9,10-dioxo-2-anthracenesulfonic acid, Na salt; Acid blue 40
CA Reg. No.: 6424-85-7
Source: Aldrich
1-Amino-9,10-dihydro-9,10-dioxo-4-[[3[[2-(sulfooxy)-ethyl]sulfonyl]phenyl]amino]-2-anthracenesulfonic acid, disodium salt; Remazol Brilliant blue R;
CA Reg. No.: 2580-78-1
Source: Aldrich
1-Amino-4[[3-[4,6-dichloro-1,3,5-triazin-2-yl)amino]-4-sulfophenyl]amino]-9,10 dihydro-9,10-dioxo-2-anthracene-sulfonic acid; reactive blue 4
CA Reg. No.: 13324-20-4
Source: Aldrich
1-(9,10-Dihydro-9,10-dioxo-1-anthracenyl-1,2-hydrazine-disulfonic acid, di Na salt; (1-Anthraquinonyl)-1,2-hydrazine disulfonic acid, di Na salt
CA Reg. No.: 54345-83-4
Source: K & K
9,10-Dihydro-5,6-dihydroxy-9,10-dioxo-1-anthracene-sulfonic acid; Alizarin-5-sulfonic acid
CA Reg. No.: 6373-42-8
Source: Tokyo Kasei Kogyo Co., Ltd.
c/o CTC Organics
792 Windsor Street
P.O. Bex 6933
Atlanta, GA 30315
N-(4-Chloro-9,10-dihydro-9,10-dioxo-1-anthracenyl)-benzamide; 1-Benzamido-4-chloroanthraquinone
CA Reg. No.: 81-45-8
Source: Aldrich -continued 1-Amino-4-bromo-9,10-dihydro-9,10-dioxo-2-anthracene-
sulfonic acid, Na salt; 1-Amino-4-bromoanthraquinone-2-
sulfonic acid, Na salt
CA Reg. No.: 6258-06-6
Source: Aldrich
1-Amino-9,10-dihydro-4[[(4-methylphenyl)sulfonyl]amino-
9,10-dioxo-2-anthracenesulfonic acid, Na salt; 1-Amino-
4-(p-toluenesulfonamido)anthraquinone-2-sulfonic acid,
Na salt
CA Reg. No.: 64981-00-6
Source: Aldrich
9,10-Dihydro-9,10-dioxo-2,3-anthracenedicarboxylic acid
CA Reg. No.: 27485-15-0
Source: Aldrich
1,1'-Iminobis(4-nitro-9,10-anthracenedione)
CA Reg. No.: 128-88-1
Source: Pfaltz & Bauer
1-Amino-4-chloro-2-methylanthraquinone
CA Reg. No.: 3225-97-6
Source: Aldrich
2,3-dimethyl-1,4-dihydroxyanthraquinone; 2,3-Dimethyl-
quinizarin
CA Reg. No.: 25060-18-8
Source: Aldrich
6-Methyl-1,3,8-trihydroxyanthraquinone; Emodin (99%)
CA Reg. No.: 518-82-1
Source: Aldrich
1,4-Bis(methylamino)-anthraquinone
CA Reg. No.: 2475-44-7
Source: Aldrich
N-(4-Amino-9,10-dihydro-3-methoxy-9,10-dioxo-1-
anthracenyl)-4-methylbenzenesulfonamide; N-(4-Amino-3-
methoxyanthraquinone-1-yl)-p-toluenesulfonamide; 1-
Amino-2-methoxy-4-(p-tolylsufonamido)anthraquinone
CA.Reg. No.: 81-68-5
Source: Aldrich
[1,1'-Bianthracene]-9,9'10,10'-tetrone; 1,1'-Bianthra-
quinone
CA Reg. No.: 914-20-5
Source: Columbia Organic Chemical Co., Inc.
P.O. Box 1045
Camden, SC 29020
6,7-Dichloro-1,4-dihydroxyanthraquinone (97%)
CA Reg. No.: 1225-15-6
Source: Aldrich
2-[[9,10-Dihydro-4-(methylamino)-9,10-dioxo-1-
anthracenyl]amino]-5-methyl-benzenesulfonic acid,
monosodium salt; Alizarine astrol B-CF
CA Reg. No.: 6408-51-1
Source: Tokyo Kasei Kogyo Co., Ltd.
2,8-Diphenyl-anthra[2,1-d:6,5-d']bisthiazole-6,12-dione;
Indanthrene yellow GCN
CA Reg. No.: 129-09-9
Source: Tokyo Kasei Kogyo Co., Ltd.
2-Methoxy-3-methyl-9,10-anthracenedione
CA Reg. No.: 17241-42-8
Source: Aldrich
1,4-Bis[(1-methylethyl)amino]-9,10-anthracenedione;
1,4-Di(isopropylamino)anthraquinone
CA Reg. No.: 14233-37-5
Source: K & K
1,4-Bis[(2,4,6-triethylphenyl)amino]-9,10-anthracene-
dione; 1,4-Bis(2,4,6-triethylanilino)anthraquinone
CA Reg. No.: 116-74-5
Source: K & K
1-(2-Hydroxyethyl)amino-4-methylaminoanthraquinone;
Disperse blue 3
CA Reg. No.: 2475-46-9
Source: Aldrich
1,4-Bis[(4-methylphenyl)amino]9,10-anthracenedione;
Solvent green 3
CA Reg. No.: 128-80-3
Source: Aldrich
2-Amino-3-hydroxyanthraquinone
CA Reg. No.: 117-77-1
Source: Tokyo Kasei Kogyo Co., Ltd.
1-(Bromothio)anthraquinone
CA Reg. No.: None
Source: Aldrich
1,8-Bis(phenylmethoxy)-9,10-anthracenedione;
1,8-Dibenzyloxyanthraquinone
CA Reg. No.: 69595-66-0

-continued

Source: Aldrich
1-Amino-2-(2-aminoethylthio)-4-hydroxyanthraquinone
CA Reg. No.: None
Source: Aldrich
1,4-Bis(pentylamino)-9,10-anthracenedione; Oil blue N
CA Reg. No.: 2646-15-3
Source: Aldrich
1-Amino-2-bromo-4-hydroxyanthraquinone
CA Reg. No.: 116-82-5
Source: Aldrich
2-Propionamidoanthraquinone
CA Reg. No.: None
Source: Aldrich
1,4-Diamino-2,3-bis(2-phenoxyethoxy)anthraquinone
CA Reg. No.: 41313-11-5
Source: Aldrich
N-(5-Chloro-9,10-dihydro-9,10-dioxo-1-anthracenyl)-
benzamide; 1-Benzamido-5-chloroanthraquinone
CA Reg. No.: 117-05-5
Source: Aldrich
Anthraquinone-1-arsonic Acid
CA Reg. No.: None
Source: K & K
N,N'-[Iminobis(9,10-dihydro-9,10-dioxo-4,1-
anthracenediyl)]-bisbenzamide; 4,4'-Dibenzamido-1,1'-
dianthrimide
CA Reg. No.: 128-79-0
Source: Aldrich
1,4,5,8-Tetraaminoanthraquinone; Disperse blue 1
CA Reg. No.: 2475-45-8
Source: Aldrich
2-Methylanthraquinone
CA Reg. No.: 84-54-8
Source: Aldrich
9,10-Dihydro-9,10-dioxo-2,7-anthracenedisulfonic acid,
di Na salt; Anthraquinone-2,7-disulfonic acid, di Na
salt
CA Reg. No.: 853-67-8
Source: K & K
1,2,3-trihydroxyanthraquinone; Anthragallol
CA Reg. No.: 602-64-2
Source: K & K
Carmine (Aluminum lake)
CA Reg. No.: 1390-65-4
Source: Fisher Scientific Co., Inc.
711 Forbes Avenue
Pittsburg, PA 15219
9,10-Dihydro-1,4-dihydroxy-9,10-dioxo-2-anthracene-
sulfonic acid
CA Reg. No.: 145-48-2
Source: Pfaltz & Bauer
2-Amino-3-chloroanthraquinone
CA Reg. No.: 84-46-8
Source: Kodak
1-Anthraquinonesulfonic acid, Na salt
CA Reg. No.: 128-56-3
Source: Kodak
2-tert-butylanthraquinone (98%)
CA Reg. No.: 84-47-9
Source: Aldrich
1,4-Dihydroxyanthraquinone
CA Reg. No.: 81-64-1
Source: Lancaster
1,5-Diamino-4,8-dihydroxyanthraquinone
CA Reg. No.: 145-49-3
Source: Lancaster
1-Hydroxy-4-[(4-methylphenyl)amino]-9,10-anthracene-
dione; 1-Hydroxy-4-(p-toluidino)-anthraquinone
CA Reg. No.: 81-48-1
Source: Sigma
1,4-Dimethylanthraquinone (95%)
CA Reg. No.: 1519-36-4
Source: Pfaltz & Bauer
1,1'-Iminobis-9,10-anthracenedione; Dianthrimide
CA Reg. No.: 82-22-4
Source: Pfaltz & Bauer
2-(Cyclopropylcarboxamido)anthraquinone
CA Reg. No.: None
Source: Aldrich
1-Amino-2-methylanthraquinone; Disperse orange 11
CA Reg. No.: 82-28-0
Source: Sigma

| -continued |
|---|
| 2-[(9,10-Dihydro-4-hydroxy-9,10-dioxo-1-anthracenyl)-amino]-5-methyl-benzenesulfonic acid, Na salt; Solway purple R |
| CA Reg. No.: 4430-18-6 |
| Source: K & K |
| 2,2'-[(9,10-Dihydro-5,8-dihydroxy-9,10-dioxo-1,4-anthracenediyl)diimino]bis[5-methyl]benzenesulfonic acid; alizarine viridine |
| CA Reg. No.: 4430-16-4 |
| Source: K & K |
| 1,4-Bis(ethylamino)-9,10-anthracenedione; Sudan blue |
| CA Reg. No.: 6994-46-3 |
| Source: K & K |
| 1,4-Diamino-5-nitroanthraquinone |
| CA Reg. No.: 82-33-7 |
| Source: K & K |
| N-Benzyl-9,10-dihydro-9,10-dioxo-2-anthracenesulfonamide |
| CA Reg. No.: None |
| Source: Aldrich |
| 2-Bromoanthraquinone |
| CA Reg. No.: 572-83-8 |
| Source: E. I. du Pont de Nemours and Company |
| 1-Fluoroanthraquinone |
| CA Reg. No.: 569-06-2 |
| Source: E. I. du Pont de Nemours and Company |
| 1-Cyanoanthraquinone |
| CA Reg. No.: 38366-32-4 |
| Source: E. I. du Pont de Nemours and Company |
| 2-Trifluoromethylanthraquinone |
| CA Reg. No.: 362-21-0 |
| Source: E. I. du Pont de Nemours and Company |

All the above-named compounds except N-[1-(9,10 dihydro-9,10 dioxo)anthracenyl]-N'-(1-methylethyl)imido dicarbonimidic diamide hydrochloride are commercially available. N-[1-(9,10 dihydro-9,10 dioxo)anthracenyl]-N'-(1-methylethyl)imido dicarbonimidic diamide hydrochloride, however, is a novel compound and was synthesized as follows: A three liter round bottomed flask was charged with 18.2 g (3.09 mole) of isopropyl amine. After cooling the flask to $-70°$ C. in a dry ice and acetone bath, 304.5 g of concentrated (37%) hydrochloric acid (3.09 mole) was added. The mixture was warmed to room temperature and water was removed with a rotary evaporator at aspirator pressure. To the dry residue was added 275.3 g (3.09 mole) of sodium dicyanamide and 760 ml of 1-butanol. The mixture was heated under reflux for three hours and then the butanol was removed with a rotary evaporator at aspirator pressure. To the residue in the flask was added 1800 ml of 1,4-dioxane. A slightly sticky precipitate was formed which was filtered and recrystallized from four liters of 1,4-dioxane to yield 379 g of N-cyano-N'-isopropylguanidine as a co-precipitate with some NaCl, 1,4-dioxane, and isopropylamine. Calc. for $C_5H_{10}N_4$ $(NaCl)0.1(C_4H_8O_2)0.1(C_3H_9N)0.15$ Calc: C 46.94; H 8.18; N 38.83; Cl 2.37 Found: C 46.85; H 8.27; N 38.42; Cl 2.44

To 5.02 g of 1-aminoanthraquinone (0.0225 mole) was added 2.22 g (0.0225 mole) of concentrated (37%) hydrochloric acid. The mixture was dried at 95° C. on a rotary evaporator to give a free-flowing powder. Then, 20 ml of 1-butanol and 4.26 g of N-cyano-N'-isopropylguanidine as prepared above were added to the flask and the mixture was refluxed for one hour. The mixture was then cooled to room temperature (about 22° C). The reaction was judged to be complete due to the absence of a cyano group infrared stretching frequency at 2180 cm$^{-1}$. The product was precipitated by adding 100 ml of diethyl ether and air dried to give 5.86 g of N-[1-(9,10 dihydro-9,10 dioxo)anthracenyl]-N'-(1-methylethyl)imido dicarbonimidic diamide hydrochloride having characteristic infrared absorption at 1640, 1601, 1540, and 1285 cm$^1$.

The preferred anthraquinones to inhibit sulfide production by sulfate-producing bacteria are: anthraquinone, 1,8-dihydroxyanthraquinone, 1-chloroanthraquinone, 2-chloroanthraquinone, 3-chloro-2-anthraquinone carboxylic acid, 2-bromoanthraquinone, 1-fluoroanthraquinone, or 1-cyanoanthraquinone. If sulfate-reducing bacteria are growing by sulfate respiration (which is the growth mode from which they derive the most energy or growth) then inhibition of sulfide production will result in cessation of bacterial growth. Cessation of bacterial growth under these conditions may not necessarily result in cell death and does not preclude the bacteria utilizing other energy yielding pathways which do not involve sulfate as an electron acceptor as previously discussed.

A number of different sulfate-reducing bacteria as well as several other organisms are suitable for use in the present invention. Preferred are *Desulfovibrio desulfuricans, D. salexigens, D. vulgaris, D. multispirans,* or *D. gigas.* Those used in the experiments of this invention were grown in BTZ-3, BTZ-3 supplemented with other chemicals, or BTZ-4 medium. These media will be described hereinafter. The organisms used in the experiments were obtained from the sources shown below but they are available from the American Type Culture Collection, 12301 Parklawn Drive, Rockville, Md. 20852. For use in the experiments below, *Desulfovibrio desulfuricans* G100A was isolated at E. I. du Pont de Nemours and Company, Wilmington, Del.; *D. desulfuricans* API was obtained from the American Petroleum Institute; *D. salexigens, D. vulgaris, D. desulfuricans* #ATCC27774 and *D. desulfuricans* Norway were obtained from the laboratory of Dr. H. D. Peck Jr. University of Georgia, Athens Ga. 30601 and were grown in BTZ-3 medium supplemented with sterile sodium lactate (60 mM) and sodium sulfate (30 mM). The *D. salexigens* and *D. desulfuricans* Norway strains were grown in BTZ-3 medium supplemented additionally with sodium chloride to a final concentration of 0.4 M. BTZ-3 medium was used to grow *Escherichia coli* and *T. denitrificans*, however, the medium was then supplemented differently for each organism to contain 5 mM glucose for *E. coli* and 25 mM sodium thiosulfate and 10 mM sodium nitrate for *T. denitrificans*. Growth conditions for all the above organisms were strictly anaerobic with a nitrogen atmosphere. Where reducing agents were added to the medium a reducing agent of the following composition was used:

| | |
|---|---|
| Sodium sulfide 9 hydrate | 50 mM |
| Cysteine hydrochloride in 0.1 N sodium hydroxide | 50 mM |

There may be a problem in delivering a known amount of an anthraquinone to an aqueous system because these compounds are not very soluble in water. Therefore solvent systems to deliver concentrated amounts of inhibitor accurately may be required. Suitable solvents for use herein comprise water-miscible solvents. Examples of such solvents include, but are not limited to, water, detergent emulsions in water, ethanol, acetone, methanol, dimethylsulfoxide, dimethylformamide, or tetrahydrofuran. Due to their aqueous insolubility, one cannot be certain that the final concentration of the compound correlates, in a linear fashion, with the amount added in the organic solvent. The water solubility of, for example, the 1,8 dihydroxyanthraquinone is 2–3 ppm, however it is demonstrated that additions of the compound in excess of this amount have additional inhibitory effect, therefore it is often necessary and beneficial to add the inhibitor in excess of its theoretical solubility.

Typically, in our experiments, the anthraquinone to be tested was dissolved to a concentration of 300 ppm in ethanol:water (80:20, 20 mM pH7 sodium phosphate buffer). This was used to deliver the compound to a growing bacterial suspension in BTZ-3 medium. While this is the preferred solvent, other solvents such as acetone, methanol-water (80:20), dimethylformamide, and tetrahydrofuran have proven to be equally efficacious. The pH of the ethanol-water system can be from 5 to 12 with no apparent pH effect. There is no reason to suspect that the compound must be delivered in the ethanol-water buffer or acetone or any particular organic solvent. In fact depending upon the particular system or anthraquinone, the solid compound could be added to it directly.

Experiments have established that the compounds are effective at a final concentration of at least 0.1 ppm. When an inhibitory anthraquinone is added to a growing culture of Desulfovibrio sp. growth and sulfide formation cease immediately at anthraquinone concentrations of 3 ppm. This cessation typically lasts for several days after which growth resumes. This effect has been demonstrated with several different species of Desulfovibrio in pure culture. It has also been found that the redox potential of the culture affects the potency of the anthraquinone. Compounds are most effective when added to a culture in early exponential growth where some sulfide has already been produced thus rendering the medium more reduced than uninoculated medium. However compounds still show some inhibition when added to oxidized medium which is subsequently inoculated. It has been shown that use of a reducing agent can enhance the strength of the inhibition even when the inhibitor is added concurrently with the inoculum. A preferred reducing agent is sodium sulfide at concentrations of between about 2 and about 4 mM in the medium. This aspect would suggest that the compounds are most effective under anaerobic, reduced conditions as would be found in, for example a sewage treatment anaerobic digestor, or in another respect the compounds may be thought of as being activated by the end-product of the sulfate-reducer which is sulfide.

This invention further comprises a process for the automated screening of inhibitors of sulfide production by bacteria. While any sulfide-producing bacterium can be used, an isolate of *Desulfvibrio desulfuricans* (strain G100 A) from an oilfield was used for the experiments described. The isolation and physiological characteristics of this strain have been described previously by Weimer et al., 1988 Appl. Environ. Microbiol. 54:386–396. The process comprises: a) maintaining a culture of sulfate-reducing bacteria in exponential growth phase by chemostat culture of the organsims; b) contacting in an automated analyzer a solution of the compound to be tested with an aliquot of said culture of step a); c) adding to the compound and culture a substrate to initiate sulfide production; d) incubating the culture, compound and substrate mixture to permit sulfide production; and e) measuring the amount of sulfide produced.

The system is shown schematiclly in FIG. 1. The candidate inhibitors are delivered from an automated sampler (1) into the bacterial culture stream (2) (the culture was freshly removed from the chemostat into a 158 ml serum vial and sparged with argon or nitrogen for about 1 hour to reduce the background sulfide level to below 0.2 mM). Immediately, small bubbles of nitrogen gas (3) are introduced into the bacterial culture/inhibitor stream to produce discrete liquid segments. After traversing this and a ten-turn mixing coil (4) (time required is about 1.6 min), substrate solution (5) (10 mM Na lactate, 5 mM $Na_2SO_4$, and from 0.1% to 0.2% final concentration using a 30% stock solution of Brij® 35(v/v) (trademark of Atlas Chemical Industries, Inc. and available from Fisher Scientific Co., Fairlawn, N.J. 07410)) is introduced into each liquid segment. The segments traverse the downstream tubing (6) in the system for about 18 minutes, at which point a small amount of 0.03N sulfuric acid (7) is added to reduce the pH to about 4.5. At this pH, sulfate reduction ceases and greater than 99% of the sulfide anions ($S^=$ and $HS^-$) are converted to $H_2S$ without lysing the bacterial cells. The $H_2S$ diffuses through a gas-permeable silicone membrane (8) and is picked up by a very dilute solution of Brij® 35 surfactant (9), which aids in maintaining the integrity of the individual liquid segments. The sulfide is next reacted with N,N-dimethyl-p-phenylenediamine sulfate or dihydrochloride (DPD,10) and ferric chloride (11) to produce methylene blue whose concentration is determined by the spectrophotometric flow cell (12) at the end of the reaction loop.

The letters A through D on FIG. 1 indicate flow rates for polyvinylchloride pump tubing of the indicated collar color as follows: A=orange/green 0.10 ml/min.; B=orange/white 0.23 ml/min.; C=black/black 0.32 ml/min.; D=red/red 0.8 ml/min. Such tubing is available from Technicon Instruments Corp., Tarrytown, N.Y., as Flow Rated Pump Tube, from Precision Technology, Inc., 375 Oaktree Rd., Palisades, N.Y., 10964 as Acculab® Flow Rated Pump Tubes, and from Elkay Products via Fisher Scientific Co., Fairlawn, N.J., 07410 as AccuRated® pump tubing. Culture, inhibitor and substrate solutions are typically added at equivalent volumes. Typical reagent concentrations used are as follows: substrate=1.12 g sodium lactate+0.71 g $Na_2SO_4$/L; DPD=N,N-dimethyl-p-phenylenediamine sulfate or dihydrochloride at 1.19 g/L in 1.14 N HCl; ferric chloride=3.1 g/L in 1.14 N HCl; surfactant=1.0 ml/L of 30% Brij®35. The letter T represents the number of turns of glass mixing coils. All parts used were standard Technicon® AutoAnalyzer II® parts available from Technicon® Instruments Corporation, 511 Benedict Avenue, Tarrytown, N.Y. 10591. Similar equipment which provides equivalent results can also be used.

In order to maintain anaerobic conditions for the bacteria and to prevent oxidation of the sulfide generated during the incubation, the entire apparatus is contained inside an anaerobic glovebag (Coy Manufacturing Co., Ann Arbor, Michigan). However, sparging of the culture vessel is to be avoided, as it reduces the background level of sulfide in the culture and thus causes baseline drift.

Figure 2:
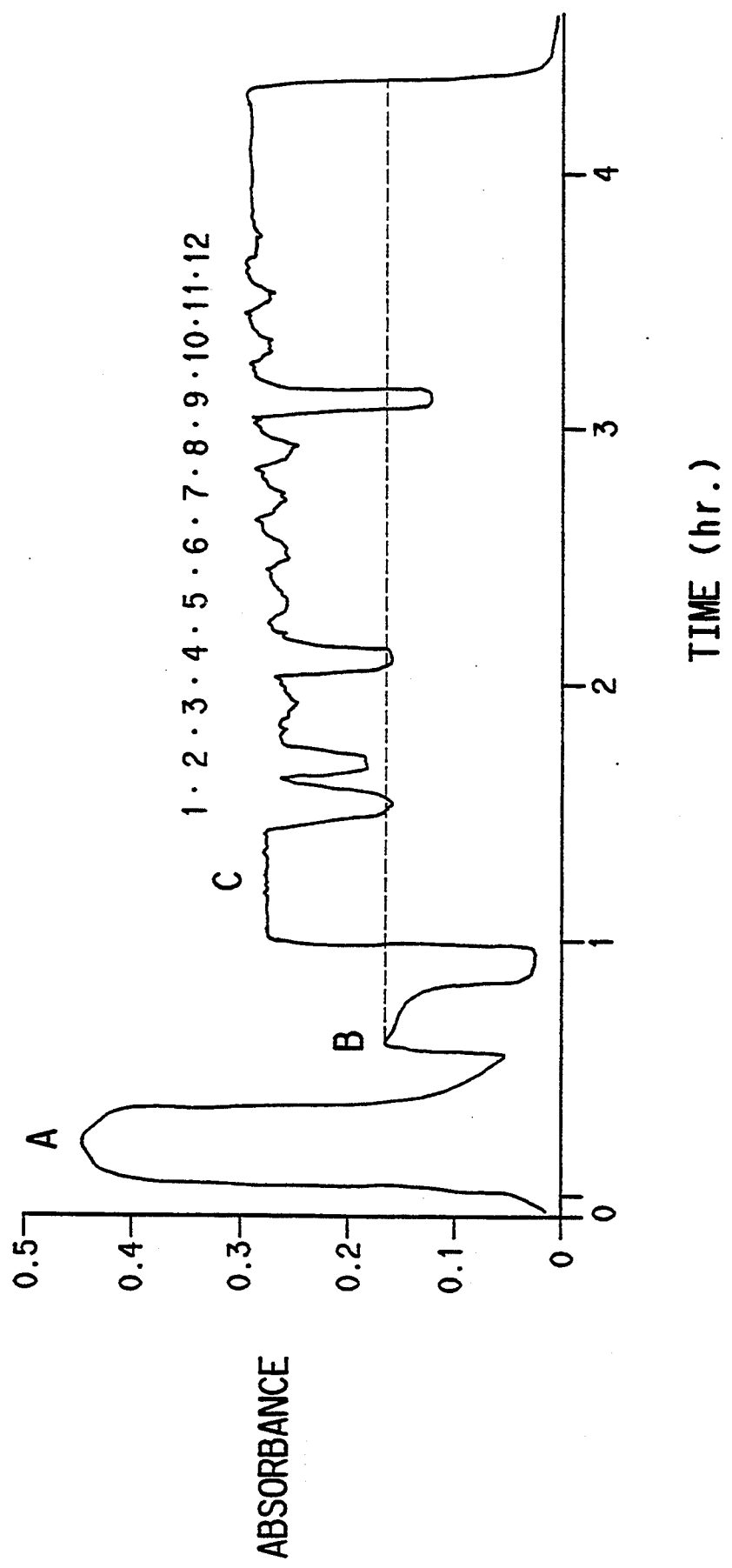
FIG. 2 is a trace from an automated analyzer used to screen anthraquinones for inhibition of sulfide production.

The net amount of sulfide produced is determined by subtracting the background amount of sulfide produced by combining fresh culture filtrate with lactate/sulfate and with water (instead of the inhibitor solution), from the amount of sulfide produced by combining culture, lactate/sulfate, and water. The culture filtrate is obtained by filtering the sparged chemostat sample described above through a 0.2 μm filter; this filtration is performed in the glovebag to prevent oxidation of the sulfide. In order to provide a baseline measure of sulfide production by uninhibited cultures, a vial of N$_2$-sparged water is inserted between each candidate inhibitor vial in the autosampler rack. Sulfide production resulting from this combination of water, culture, and lactate/sulfate represents the amount of sulfide produced by the uninhibited culture. A typical chart trace from an AutoAnalyzer® run is shown in FIG. 2. A indicates the 0.45 mM sodium sulfide standard plus lactate/sulfate plus water. B is the culture filtrate plus lactate/sulfate plus water. C is the cell suspension plus lactate/sulfate plus water. The numbers 1 through 12 indicate different test compounds plus cell suspension with substrate. The points indicated by a dot above each downward-tending peak represent the level of sulfide in uninhibited cultures. Note that the inclusion of a water vial between each candidate inhibitor provides a convenient marker for determining the amount of inhibition obtained for each compound. The extent of inhibition of sulfide is calculated as follows:

$$\% \text{ inhibition} = 1 - \frac{\text{net mM sulfide in presence of inhibitor}}{\text{net mM sulfide in absence of inhibitor}} \times 100$$

Because the automated assay is based upon the measurement of sulfide production, test compounds which react with sulfide (whether by oxidation, complexation, or precipitation) will underestimate the net amount of sulfide formed and thus overestimate the extent of inhibition. The detection of such reactivity can usually be accomplished by the assay method if the cell suspension used has a moderate background level of sulfide; reactive compounds will often yield a sulfide peak below that obtained from the filtrate itself (FIG. 2, peak 9), particularly if the candidate inhibitor is tested at relatively high concentration. However, it is essential that all compounds which appear to cause a net decrease in sulfide formation be retested for their reactivity with sulfide in the absence of active cells. This is most easily accomplished by using an automated analyzer to combine test compound, lactate/sulfate, and (instead of a bacterial suspension) a standard solution (e.g., 0.5 mM) of sodium sulfide. Reaction with sulfide is detected as a decrease in methylene blue formation that is detected by the spectrophotometer.

Under normal operating conditions, the instrument's recording chart is set such that full scale was equivalent to either 0.5 or 1.0 mM sulfide. A steady chart trace permits the detection of changes in sulfide production of 5 to 10 μM (0.01 X full scale absorbance). The relative sensitivity could be enhanced even further by increasing the total amount of sulfide formed (e.g., by lengthening the reaction path).

The screen has been used to test a wide variety of compounds for their ability to inhibit bacterial sulfide production. It has also been used to evaluate promising inhibitors with respect to concentration effects and to retention or loss of inhibitory activity following exposure to environmental stresses (e.g., extremes of temperature or salinity). The automated nature of the method permits unattended operation and maximizes sample throughput (particularly if a 144-sample automated sampler tray is used) while retaining the high degree of reproducibility afforded by the use of chemostat-grown cells. The method has been effective in rapidly identifying compounds which inhibit sulfide production by sulfate-reducing bacteria. The enhanced reproducibility of the assay method resulting from the use of chemostat-grown bacteria is in agreement with the report of Lagarde et al., 1976 Corrosion, Traitments, Protection, Finition 15: 275-280, who screened inhibitors by determining changes in bacterial cell density and sulfide production following direct addition of test compounds to chemostats containing sulfate-reducing bacteria. While their method provided reproducible data, it is not practical for screening large numbers of compounds, due to the limited number of chemostats that can be maintained simultaneously, and to the long time required to re-establish steady-state biological and chemical conditions following addition of inhibitor.

The following Examples showing the results of the screening process (i.e., inhibition of sulfide production) and other aspects of the inhibition of sulfide production by anthraquinones illustrate the present invention but are not intended to limit it in any way.

EXAMPLE 1

Screening Anthraquinones for Inhibition of Sulfide Production by Desulfovibrio desulfuricans G100A A culture of *Desulfovibrio desulfuricans* G100A was maintained in exponential growth phase by chemostat culture of the organism. The organism was maintained in a single stage chemostat (working volume=1 liter) continuously fed BTZ-4 medium which is BTZ-3 medium modified to contain 40 mM sodium lactate as growth limiting nutrient, and a reduced (to 0.05 mM) level of ferrous iron. The medium designated BTZ-3 consisted of the following mineral base:

| | |
|---|---|
| Ammonium sulfate | 5.3 g |
| Potassium dihydrogen phosphate | 0.68 g |
| (or Dipotassium hydrogen phosphate | 0.087 g) |
| Magnesium sulfate heptahydrate | 0.2 g |
| Calcium chloride dihydrate | 0.1 g |
| Mineral solution 10X, | 1.0 ml |
| Iron sulfate heptahydrate | 0.0042 g |
| Deionized water to a final volume of 1 liter | |
| Composition of 10X mineral solution: | |
| Nitrilotriacetic acid | 12.8 g |
| Cupric chloride 2H$_2$O | 0.254 g |
| Manganese chloride 4H$_2$O | 1.0 g |
| Cobalt chloride 6H$_2$O | 3.115 g |
| Zinc chloride | 1.0 g |
| Boric acid | 0.1 g |
| Sodium molybdate 2H$_2$O | 0.1 g |
| Nickel chloride 6H$_2$O | 1.84 g |
| Deionized water to 1000 ml | |
| pH to 7.0 | |

The chemostat was operated at ambient temperature (19° to 24° C.), pH 7.9 to 8.2, and a dilution rate of 0.035 per hour. Bacterial concentrations (as determined by direct counting in a Petroff-Hauser counting chamber and a phase contrast microscope) consistently fell between 7 and 9×10$^8$ cells per ml. The automated screen in this example used a Technicon® AutoAnalyzer® II as both an incubator to expose chemostat-grown bacteria to different inhibitors in the presence of bacterial growth substrates (lactate and sulfate), and as an analyzer of the amount of H$_2$S formed as a consequence of the incubation. Thus compounds were each tested with bacteria of the same strain at about the same bacterial cell density (i.e., 7–9×10$^8$ cells/ml) and the same stage of growth (exponential). Compounds were prepared as 300 ppm solutions in ethanol:aqueous:phosphate buffer (80:20, 20 mM Phosphate pH 7). After solubilizing the compound in this solution, the solution was diluted 10 fold and an aliquot placed in the AutoAnalyzer ®. Introduction of the aliquot of compound into the bacterial suspension resulted in another 3 fold dilution and thus compounds were actually exposed to the cells at 10 ppm (theoretical) concentration with 2.7% ethanol and 0.7 mM phosphate present. Controls with solvent only (minus compound to be tested) were run for each compound tested. An additional control used was chlorhexidine, a potent non-specific bacteriocide which also inhibits sulfide production. Inhibition by this compound was an indicator of the overall reproducibility of the assay and results were expressed both as total percent inhibition of sulfide production and inhibition relative to chlorhexidine inhibtion.

In the AutoAnalyzer ® compounds were mixed with the bacterial suspension and incubated for approximately 1.6 minutes at which time the substrates for sulfide production were added (10 mM sodium lactate and 5 mM sodium sulfate). This mixture was then incubated for an additional 18 minutes to allow the formation of sulfide. The reaction was stopped by volatilizing the formed sulfide with a small amount of sulfuric acid and measuring the formed sulfide as described in detail above. The resulting data are summarized in Table I.

In Table I, the notation "<10 ppm" indicates that the compound was not totally soluble upon visual inspection of the sampling vials at a concentration of 30 ppm in 8% EtOH prior to the 3x dilution by the analyzer. The notation "<<10 ppm" indicates that there was very little solubility upon visual inspection of the sampling vials at a concentration of 30 ppm in 8% EtOH prior to the 3x dilution by the analyzer.

TABLE I

| Compound: | N-[1-(9,10-dihydro-9,10-dioxo)anthracenyl]-N'-(1-methylethyl)imidodicarbonimidic diamide hydrochloride |
|---|---|
| % Inhib. | 83.1% (10 μM-3% ETOH,) |
| Compound: | 1-Aminoanthraquinone (97%) |
| % Inhib. | 28.4% @ 10 ppm in 2.7% ETOH |
| Compound: | 2-Aminoanthraquinone |
| % Inhib. | 30.4% @ 10 ppm in 2.7% ETOH |
| Compound: | 1-Amino-4-hydroxyanthraquinone |
| % Inhib. | 54.3% @ <10 ppm in 2.7% ETOH |
| Compound: | 1,2-Diaminoanthraquinone |
| % Inhib. | 28.9% @ 10 ppm in 2.7% ETOH |
| Compound: | 2,6-Dihydroxyanthraquinone; Anthraflavic acid |
| % Inhib. | 28.2% @ 10 ppm in 2.7% ETOH |
| Compound: | Anthraquinone-2-carboxylic acid (98%) |
| % Inhib. | 22.6% @ <10 ppm |
| Compound: | 1,5-Dihydroxyanthraquinone; Anthrarufin (92%) |
| % Inhib. | 31.0% @ 10 ppm in 2.7% ETOH |
| Compound: | 1,2-Dihydroxyanthraquinone; Alizarin |
| % Inhib. | 68.9% @ 10 ppm, in 2.7% ETOH |
| Compound: | 2,2'-[(9,10-Dihydro-9,10-dioxo-1,5-anthracenediyl)-diimino]bis[5-methylbenzenesulfonic acid], di Na salt; Alizarin violet 3R |
| % Inhib. | 30.9% @ 10 ppm |
| Compound: | 1,2,5,8-Tetrahydroxyanthraquinone; Quinalizarin |
| % Inhib. | 80% @ 10 ppm in 2.7% ETOH |
| Compound: | 4-Amino-9,10-dihydro-1,3-dihydroxy-9,10-dioxo-2-anthracenesulfonic acid, monosodium salt; Nuclear fast red |
| % Inhib. | 20.4% @ 10 ppm |
| Compound: | 1,8-Dihydroxyanthraquinone; Danthron |
| % Inhib. | 82.2% @ 10 ppm in 2.7% ETOH |
| Compound: | 2,2'-[(9,10-Dihydro-9,10-dioxo-1,4-anthracenediyl)-diimino]bis[5-methylbenzenesulfonic acid],di Na salt; Acid green 25 |
| % Inhib. | 38.8% @ 10 ppm |

TABLE I-continued

| Compound: | 1-Amino-2,4-dibromoanthraquinone |
|---|---|
| % Inhib. | 44.6% @ 10 ppm in 2.7% ETOH |
| Compound: | 5-Chloro-1-aminoanthraquinone |
| % Inhib. | 57.1% @ 10 ppm in 2.7% ETOH |
| Compound: | 2-Ethylanthraquinone (97+%) |
| % Inhib. | 57.1% @ approx. 10 ppm in 2.7% ETOH |
| Compound: | 1-Hydroxyanthraquinone (97%) |
| % Inhib. | 59.3% @ 10 ppm in 2.7% ETOH |
| Compound: | 2-(Hydroxymethyl)anthraquinone (97%) |
| % Inhib. | 87% @ <10 ppm in 2.7% ETOH |
| Compound: | 1-Amino-4-methoxyanthraquinone |
| % Inhib. | 57.1% @ 10 ppm in 2.7% ETOH |
| Compound: | 1-Amino-6,7-dichloroanthraquinone |
| % Inhib. | 22.9% @ <10 ppm in 2.7% ETOH |
| Compound: | Benz[a]anthracene-7,12-dione (97%) |
| % Inhib. | 52.9% @ <10 ppm in 2.7% ETOH |
| Compound: | 1,8-Dihydroxy-3-methylanthraquinone; Chrysophanic acid |
| % Inhib. | 27.9% @ <10 ppm in 2.7% ETOH |
| Compound: | 10-[(3-Amino-2,3,6-trideoxy-alpha-L-lyxo-hexopyranosyl)oxy]-7,8,9,10-tetrahydro-6,8,11-trihydroxy-8-(hydroxyacetyl)-1-methoxy-5,12-naphthacenedione hydrochloride; Adriamycin hydrochloride |
| % Inhib. | 55.7% @ <10 ppm in 2.7% ETOH |
| Compound: | 9,10-Dihydro-4,5-dihydroxy-9,10-dioxo-2-anthracenecarboxylic acid; Rhein |
| % Inhib. | 48.6% @ <10 ppm in 2.7% ETOH |
| Compound: | (8S-cis)-8-Acetyl-10[(3-amino-2,3,6-trideoxy-alpha-L-lyxo-hexopyranosyl)oxy]-7,8,9,10-tetrahydro-6,8,11-trihydroxy-1-methoxy-5,12-naphthacenedione hydrochloride; Daunomycin hydrochloride |
| % Inhib. | 62.9% @ <10 ppm in 2.7% ETOH |
| Compound: | 1,2,4-Trihydroxyanthraquinone; Purpurin |
| % Inhib. | 55.7% @ <10 ppm in 2.7% ETOH |
| Compound: | 1-Aminoanthraquinone diazonium salt |
| % Inhib. | 20.8% @ <10 ppm in 2.7% ETOH |
| Compound: | 2,2'-Dimethyl-[1,1'-bianthracene]-9,9',10,10'-tetrone; 2,2'-Dimethyl-1,1'-bianthraquinone |
| % Inhib. | 59.7% @ <10 ppm in 2.7% ETOH |
| Compound: | 3-(D-apio-beta-D-Furanosyloxy)-1,8-dihydroxy-6-methyl-9,10-anthracenedione; Frangulin B |
| % Inhib. | 57.1% @ <10 ppm in 2.7% ETOH |
| Compound: | 2-Chloroanthraquinone (99%) |
| % Inhib. | 98.7% @ <<10 ppm in 2.7% ETOH |
| Compound: | 1,5-Dichloroanthraquinone (96%) |
| % Inhib. | 100% @ <<10 ppm in 2.7% ETOH |
| Compound: | 1,4,5,8-Tetrachloroanthraquinone |
| % Inhib. | 50.6% @ <<10 ppm in 2.7% ETOH |
| Compound: | 1-Chloroanthraquinone |
| % Inhib. | 20.8% @ <10 ppm in 2.7% ETOH |
| Compound: | 1,8-Dichloroanthraquinone (97%) |
| % Inhib. | 3.9% @ <10 ppm in 2.7% ETOH |
| Compound: | 2-Bromo-3-methylanthraquinone |
| % Inhib. | 26.0% @ <<10 ppm in 2.7% ETOH |
| Compound: | 2-(2,2,2-Trimethylpropionamido)anthraquinone |
| % Inhib. | 48.1% @ <10 ppm in 2.7% ETOH |
| Compound: | 2,6-Bis[2-(dimethylamino)ethoxy]-9,10-anthracenedione; Tilorone analog R11,043DA |
| % Inhib. | 98.7% @ 10 ppm in 2.7% ETOH |
| Compound: | 2-Methyl-1-nitroanthraquinone |
| % Inhib. | 50% @ <<10 ppm in 2.7% ETOH |
| Compound: | 1-Amino-9,10-dihydro-9,10-dioxo-2-anthracenesulfonic acid; 1-Aminoanthraquinone-2-sulfonic acid |
| % Inhib. | 37.5% @ <10 ppm in 2.7% ETOH |
| Compound: | 9,10-Dihydro-5-nitro-9,10-dioxo-1-anthracenesulfonic acid; 5-Nitroanthraquinone-1-sulfonic acid |
| % Inhib. | 66% @ 10 ppm in 2.7% ETOH |
| Compound: | 3-Chloro-9,10-dihydro-9,10-dioxo-2-anthracenecarboxylic acid; 2-Chloroanthraquinone-3-carboxylic acid |
| % Inhib. | 100% @ 10 ppm in 2.7% ETOH |
| Compound: | 50/50 Mixture of Anthrarufin and Danthron CA Reg. No.: None |
| % Inhib. | 62.5% @ 5 ppm in 2.7% ETOH |
| Compound: | Anthraquinone |
| % Inhib. | 37.5% @ 10 ppm in 2.7% ETOH |
| Compound: | 1,8-Dihydroxy-3-(hydroxymethyl)-anthraquinone; Aloe-emodin |
| % Inhib. | 43.8% @ 10 ppm in 2.7% ETOH |
| Compound: | 7,16-Dichloro-6,15-dihydro-5,9,14,18-anthrazinetetrone; 7,16-Dichloroindanthrone |
| % Inhib. | 43.8% @ 10 ppm in 2.7% ETOH |

TABLE I-continued

| | |
|---|---|
| Compound: | 1,2,3,4,5,8-Hexahydroxyanthraquinone; Alizarin cyanin |
| % Inhib. | 40.6% @ 10 ppm in 2.7% ETOH |
| Compound: | 2,4,5,7-Tetrabromo-1,8-dihydroxy-9,10-anthracenedione; 2,4,5,7-Tetrabromochrysazin |
| % Inhib. | 40.6% @ 10 ppm in 2.7% ETOH |
| Compound: | 1,2,7-Trihydroxyanthraquinone; Anthrapurprin |
| % Inhib. | 37.5% @ 10 ppm in 2.7% ETOH |
| Compound: | 1,4,5-Trihydroxy-2-methyl-9,10-anthracenedione; Islandicin |
| % Inhib. | 50% @ 10 ppm in 2.7% ETOH |
| Compound: | 1,4,5,7-Tetrahydroxy-2-methyl-9,10-anthracenedione; Catenarin |
| % Inhib. | 37.5% @ 10 ppm in 2.7% ETOH |
| Compound: | 1,8-Dihydroxy-3-methoxy-6-methyl-9,10-anthracenedione; Physcion |
| % Inhib. | 34.4% @ 10 ppm in 2.7% ETOH |
| Compound: | 1,4,5,8-Tetrahydroxy-2-methyl-9,10-anthracenedione; Cynodontin |
| % Inhib. | 34.4% @ 10 ppm in 2.7% ETOH |
| Compound: | 1,5,8-Trihydroxy-3-methyl-9,10-anthracenedione; Helminthosporin |
| % Inhib. | 31.3% @ 10 ppm in 2.7% ETOH |
| Compound: | 1-Hydroxy-2-[(6-O-β-D-xylopyranosyl-β-D-glucopyranosyl)oxy]-9,10-anthracenedione; Ruberythric acid |
| % Inhib. | 29.7% @ 10 ppm in 2.7% ETOH |
| Compound: | 2-Phenoxy quinizarin-3,4'-disulfonic acid, di K salt |
| % Inhib. | 28.1% @ 10 ppm in 2.7% ETOH |
| Compound: | (+,−)-1-Acetoxy-8-hydroxy-1,4,4a,9a-tetrahydroanthraquinone |
| % Inhib. | 28.1% @ 10 ppm in 2.7% ETOH |
| Compound: | 1-Amino-4-[[(dimethylamino)methyl]phenyl]amino-9,10-anthracenedione; Basic Blue 47 |
| % Inhib. | 37.2% @ 10 ppm in 2.7% ETOH |
| Compound: | 1,5-Bis(2-carboxyanilino)-9,10-anthracenedione; Acridylic acid |
| % Inhib. | 33.5% @ 10 ppm in 2.7% ETOH |
| Compound: | 1,8-Dihydroxy-9-anthranol; 1,8-Dihydroxyanthranol |
| % Inhib. | 88.3% @ <10 ppm in 2.7% ETOH |
| Compound: | 1,2,10-Anthracenetriol; Anthrarobin |
| % Inhib. | 44.4% @ 10 ppm in 2.7% ETOH |
| Compound: | 1-Amino-4-bromo-2-methylanthraquinone (99%) |
| % Inhib. | 8% @ <10 ppm in 2.7% ETOH |
| Compound: | 1,4-Diaminoanthraquinone (97%) |
| % Inhib. | 27.5% @ 10 ppm in 2.7% ETOH |
| Compound: | 2,6-Diaminoanthraquinone |
| % Inhib. | 27.2% @ 10 ppm in 2.1% ETOH |
| Compound: | 1-Amino-4[4-[[4-chloro-6[2,3 or 4-sulfophenyl]-amino]-1,3,5-triazin-2-yl]amino]-3-sulfophenyl]-amino]-9,10-dihyro-9,10-dioxo-2-anthracenesulfonic acid; Procion blue HB(S); Reactive blue 2; Cibacron blue 3G-A; Basilen blue E-3G |
| % Inhib. | 17.5% @ 10 ppm |
| Compound: | Anthraquinone-1,5-disulfonic acid di Na salt hydrate (95%) |
| % Inhib. | 17.5 % @ 10 ppm |
| Compound: | Anthraquinone-2,6-disulfonic acid di Na salt |
| % Inhib. | 9.8% @ 10 ppm |
| Compound: | Anthraquinone-2-sulfonic acid sodium salt monohydrate |
| % Inhib. | 17% @ 10 ppm |
| Compound: | 1,2-Bis[(4-sulfophenyl)amino]-4-hydroxy-anthraquinone; Alizarin blue black B |
| % Inhib. | 17.5% @ 10 ppm |
| Compound: | (3,4-dihydroxy-2-anthraquinonyl)-methyliminodiacetic acid; 3-aminomethylizarin-N,N-diacetic acid; Alizarin complexone dehydrate |
| % Inhib. | 14.3% @ <10 ppm in 2.7% ETOH |
| Compound: | 1-Amino-4-([3-(ethenylsulfonyl)phenyl]-9,10-dihydro-9,10-dioxol-2-anthracene sulfonic acid, monosodium salt; Acid blue 215 |
| % Inhib. | 19.7% @ 10 ppm |
| Compound: | 1-(Methylamino)anthraquinone (98%) |
| % Inhib. | 19.1% @ <10 ppm. |
| Compound: | 2,2'-[(9,10-Dihydro-5,8-dihydroxy-9,10-dioxo-1,4-anthracendiyl)diimino]bis[5-methylbenzenesulfonic acid], di Na salt; Acid green 41 |
| % Inhib. | 17.8% @ 10 ppm |
| Compound: | 2,2'-[(9,10-Dihydro-9,10-dioxo-1,4-anthracenediyl)-diimino]bis[5-butylbenzenesulfonic acid]; Acid green 27 |
| % Inhib. | 16.5% @ 10 ppm |
| Compound: | 1,1-Iminobis[4-amino]9,10-anthracenedione, sulfonated; Acid black 48 |
| % Inhib. | 13.8% @ 10 ppm |
| Compound: | 1-Amino-9,10-dihydro-9,10-dioxo-4-(phenylamino)-2-anthracenesulfonic acid, Na salt; Acid blue 25 |
| % Inhib. | 26% @ 10 ppm in 2.7% ETOH |
| Compound: | 4-[[4-(Acetylamino)phenyl]amino]-1-amino-9,10-dihydro-9,10-dioxo-2-anthracenesulfonic acid, Na salt; Acid blue 40 |
| % Inhib. | 12.5% @ 10 ppm |
| Compound: | 1-Amino-9,10-dihydro-9,10-dioxo-4-[[3[[2-(sulfoxy)-ethyl]sulfonyl]phenyl]amino]-2-anthracenesulfonic acid, disodium salt; Remazol Brilliant blue R; |
| % Inhib. | 12.4% @ 10 ppm |
| Compound: | 1-Amino-4-[3-[4,6-dichloro-1,3,5-triazin-2-yl)amino]-4-sulfophenyl]amino]-9,10 dihydro-9,10-dioxo-2-anthracenesulfonic acid; reactive blue 4; |
| % Inhib. | 7.3% @ 10 ppm |
| Compound: | 1-(9,10-Dihydro-9,10-dioxo-1-anthraceny)-1,2-hydrazinedisulfonic acid, di Na salt; (1-Anthraquinonyl)-1,2-hydrazine disulfonic acid, di Na salt |
| % Inhib. | 10% @ 10 ppm in 2.7% ETOH |
| Compound: | 9,10-Dihydro-5,6-dihydroxy-9,10-dioxo-1-anthracenesulfonic acid; Alizarin-5-sulfonic acid |
| % Inhib. | 7.1% @ <10 ppm in 2.7% ETOH |
| Compound: | N-(4-Chloro-9,10-dihydro-9,10-dioxo-1-anthracenyl)-benzamide; 1-Benzamido-4-chloroanthraquinone |
| % Inhib. | 8.6% @ <10 ppm in 2.7% ETOH |
| Compound: | 1-Amino-4-bromo-9,10-dihydro-9,10-dioxo-2-anthracene-sulfonic acid, Na salt; 1-Amino-4-bromoanthraquinone-2-sulfonic acid, Na salt |
| % Inhib. | 4.3% @ 10 ppm in 2.7% ETOH |
| Compound: | 1-Amino-9,10-dihydro-4[[(4-methylphenyl)sulfonyl]-amino]-9,10-dioxo-2-anthracenesulfonic acid, Na salt; 1-Amino-4-(p-toluenesulfonamido)anthraquinone-2-sulfonic acid, Na salt |
| % Inhib. | 3.9% @ 10 ppm in 2.7% ETOH |
| Compound: | 9,10-Dihydro-9,10-dioxo-2,3-anthracenedicarboxylic acid |
| % Inhib. | 10% @ <10 ppm in 2.7% ETOH |
| Compound: | 1,1'-Iminobis(4-nitro-9,10-anthracenedione) |
| % Inhib. | 5.7% @ <10 ppm in 2.7% ETOH |
| Compound: | 1-Amino-4-chloro-2-methylanthraquinone |
| % Inhib. | 5.2% @ <10 ppm in 2.7% ETOH |
| Compound: | 2,3-dimethyl-1,4-dihydroxyanthraquinone; 2,3-Dimethylquinizarin |
| % Inhib. | 5.7% @ <10 ppm in 2.7% ETOH |
| Compound: | 6-Methyl-1,3,8-trihydroxyanthraquinone; Emodin 99% |
| % Inhib. | 2.6% @ <10 ppm in 2.7% ETOH |
| Compound: | 1,4-Bis(methylamino)-anthraquinone |
| % Inhib. | 8.6% @ <10 ppm in 2.7% ETOH |
| Compound: | N-(4-Amino-9,10-dihydro-3-methoxy-9,10-dioxo-1-anthracenyl)-4-methylbenzenesulfonamide; N-(4-Amino-3-methoxyanthraquinone-1-yl)-p-toluenesulfonamide; 1-Amino-2-methoxy-4-(p-tolylsufonamido)anthraquinone |
| % Inhib. | 4.3% @ <10 ppm in 2.7% ETOH |
| Compound: | [1,1'-Bianthracene]-9,9'10,10'-tetrone; 1,1'-Bianthraquinone |
| % Inhib. | 12.9% @ <10 ppm in 2.7% ETOH |
| Compound: | 6,7-Dichloro-1,4-dihydroxyanthraquinone 97% |
| % Inhib. | 5.7% @ <10 ppm in 2.7% ETOH |
| Compound: | 2-[[9,10-Dihydro-4-(methylamino)-9,10-dioxo-1-anthracenyl]amino]-5-methyl-benzenesulfonic acid, monosodium salt; Alizarine astrol B-CF |
| % Inhib. | 2.6% @ 10 ppm in 2.7% ETOH |
| Compound: | 2,8-Diphenyl-anthra[2,1-d:6,5-d']bisthiazole-6,12-dione; Indanthrene yellow GCN |
| % Inhib. | 15.6% @ 10 ppm in 2.7% ETOH |
| Compound: | 2-Methoxy-3-methyl-9,10-anthracenedione |
| % Inhib. | 5.0% @ <10 ppm in 2.7% ETOH |
| Compound: | 1,4-Bis[(1-methylethyl)amino]-9,10-anthracenedione; 1,4-Di(isopropylamino)anthraquinone |
| % Inhib. | 5.0% @ <10 ppm in 2.7% ETOH |
| Compound: | 1,4-Bis[(2,4,6-triethylphenyl)amino]-9,10-anthracenedione; 1,4-Bis(2,4,6-triethylanilino)anthraquinone |
| % Inhib. | 4.3% @ <10 ppm in 2.7% ETOH |
| Compound: | 1-(2-Hydroxyethyl)amino-4-methylaminoanthraquinone; Disperse blue 3 |

TABLE I-continued

| | |
|---|---|
| % Inhib. | 6.4% @ <10 ppm in 2.7% ETOH |
| Compound: | 1,4-Bis[(4-methylphenyl)amino]9,10-anthracenedione; Solvent green 3 |
| % Inhib. | 4.3% @ <10 ppm in 2.7% ETOH |
| Compound: | 2-Amino-3-hydroxyanthraquinone |
| % Inhib. | 11.4% @ <10 ppm in 2.7% ETOH |
| Compound: | 1-(Bromothio)anthraquinone |
| % Inhib. | 6.5% @ <10 ppm in 2.7% ETOH |
| Compound: | 1,8-Bis(phenylmethoxy)-9,10-anthracenedione; 1,8-Dibenzyloxyanthraquinone |
| % Inhib. | 4.5% @ <10 ppm in 2.7% ETOH |
| Compound: | 1-Amino-2-(2-aminoethylthio)-4-hydroxyanthraquinone |
| % Inhib. | 24.7% @ <10 ppm in 2.7% ETOH |
| Compound: | 1,4-Bis(pentylamino)-9,10-anthracenedione; Oil blue N |
| % Inhib. | 3.6% @ <10 ppm in 2.7% ETOH |
| Compound: | 1-Amino-2-bromo-4-hydroxyanthraquinone |
| % Inhib. | 6.5% @ <10 ppm in 2.7% ETOH |
| Compound: | 2-Propionamidoanthraquinone |
| % Inhib. | 10.4% @ <10 ppm in 2.7% ETOH |
| Compound: | 1,4-Diamino-2,3-bis(2-phenoxyethoxy)anthraquinone |
| % Inhib. | 7.8% @ <10 ppm in 2.7% ETOH |
| Compound: | N-(5-Chloro-9,10-dihydro-9,10-dioxo-1-anthracenyl)-benzamide; 1-Benzamido-5-chloroanthraquinone |
| % Inhib. | 10.4% @ <10 ppm in 2.7% ETOH |
| Compound: | Anthraquinone-1-arsonic Acid |
| % Inhib. | 18.2% @ <10 ppm in 2.7% ETOH |
| Compound: | N,N'-[Iminobis(9,10-dihydro-9,10-dioxo-4,1-anthracenediyl)]bisbenzamide; 4,4'-Dibenzamido-1,1'-dianthrimide |
| % Inhib. | 5.2% @ <10 ppm in 2.7% ETOH |
| Compound: | 1,4,5,8-Tetraaminoanthraquinone; Disperse blue 1 |
| % Inhib. | 3.9% @ <10 ppm in 2.7% ETOH |
| Compound: | 2-Methylanthraquinone |
| % Inhib. | 10.4% @ <10 ppm in 2.7% ETOH |
| Compound: | 9,10-Dihydro-9,10-dioxo-2,7-anthracenedisulfonic acid, di Na salt; Anthraquinone-2,7-disulfonic acid, di Na salt |
| % Inhib. | 9.1% @ <10 ppm 2.7% ETOH |
| Compound: | 1,2,3-trihydroxyanthraquinone; Anthragallol |
| % Inhib. | 2.6% @ <10 ppm in 2.7% ETOH |
| Compound: | Carmine (Aluminum lake) |
| % Inhib. | 7.8% @ <10 ppm in 2.7% ETOH |
| Compound: | 9,10-Dihydro-1,4-dihydroxy-9,10-dioxo-2-anthracene-sulfonic acid |
| % Inhib. | 7.8% @ <10 ppm in 2.7% ETOH |
| Compound: | 2-Amino-3-chloroanthraquinone |
| % Inhib. | 3.9% @ <10 ppm in 2.7% ETOH |
| Compound: | 1-Anthraquinonesulfonic acid, Na salt |
| % Inhib. | 3.9% @ <10 ppm in 2.7% ETOH |
| Compound: | 2-tert-butylanthraquinone (98%) |
| % Inhib. | 5.2% @ <10 ppm in 2.7% ETOH |
| Compound: | 1,4-Dihydroxyanthraquinone |
| % Inhib. | 5.2% @ <10 ppm in 2.7% ETOH |
| Compound: | 1,5-Diamino-4,8-dihydroxyanthraquinone |
| % Inhib. | 2.6% @ <10 ppm in 2.7% ETOH |
| Compound: | 1-Hydroxy-4-[(4-methylphenyl)amino]-9,10-anthracene-dione; 1-Hydroxy-4-(p-toluidino)-anthraquinone |
| % Inhib. | 3.9% @ <10 ppm in 2.7% ETOH |
| Compound: | 1,4-Dimethylanthraquinone (95%) |
| % Inhib. | 5.2% @ <10 ppm in 2.7% ETOH |
| Compound: | 1,1'-Iminobis-9,10-anthracenedione; Dianthrimide |
| % Inhib. | 2.6% @ <10 ppm in 2.7% ETOH |
| Compound: | 2-(Cyclopropylcarboxamido)anthraquinone |
| % Inhib. | 2.6% @ <10 ppm in 2.7% ETOH |
| Compound: | 1-Amino-2-methylanthraquinone; Disperse orange 11 |
| % Inhib. | 5.2% @ <10 ppm in 2.7% ETOH |
| Compound: | 2-[(9,10-Dihydro-4-hydroxy-9,10-dioxo-1-anthracenyl)-amino]-5-methyl-benzenesulfonic acid, Na salt; Solway purple R |
| % Inhib. | 9.1% @ <10 ppm in 2.7% ETOH |
| Compound: | 2,2'-[(9,10-Dihydro-5,8-dihydroxy-9,10-dioxo-1,4-anthracenediyl)diimino]bis[5-methyl]benzenesulfonic acid; alizarine viridine |
| % Inhib. | 2.6% @ <10 ppm in 2.7% ETOH |
| Compound: | 1,4-Bis(ethylamino)-9,10-anthracenedione; Sudan blue |
| % Inhib. | 1.3% @ <10 ppm in 2.7% ETOH |
| Compound: | 1,4-Diamino-5-nitroanthraquinone |
| % Inhib. | 2.7-3% @ <10 ppm in 2.7% ETOH |
| Compound: | N-Benzyl-9,10-dihydro-9,10-dioxo-2-anthracene-sulfonamide |
| % Inhib. | 3.9% @ <10 ppm in 2.7% ETOH |

EXAMPLE 2

Anthraquinones which do not inhibit sulfide production

The compounds listed in Table II were tested for inhibition of sulfide production as in Example 1 and were found not to be effective inhibitors. The notation "<10 ppm" is as previously defined in Example 1.

TABLE II

| | |
|---|---|
| Compound: | 3,4-Dihydroxy-9,10-dioxo-2-anthracenesulfonic acid; Alizarin red S monohydrate |
| CA Reg. No.: | 130-22-3 |
| % Inhib. | 0 @ 10 ppm |
| Source: | Aldrich |
| Compound: | 4-[[4-Acetylmethylamino)phenyl]amino]-1-amino-9,10-dihydro-9,10-dioxo-2-anthracenesulfonic acid, Na salt; Acid blue 41 |
| CA Reg. No.: | 2666-17-3 |
| % Inhib. | 0 @ 10 ppm |
| Source: | Aldrich |
| Compound: | 4,8-Diamino-9,10-dihydro-1,5-dihydroxy-9,10-dioxo-2,6-anthracenedisulfonic acid, di Na salt; Acid blue 45 |
| CA Reg. No.: | 2861-02-1 |
| % Inhib. | 0 @ 10 ppm |
| Source: | Aldrich |
| Compound: | 3,31-[(9,10-Dihydro-9,10-dioxo-1,4-anthracenediyl)adiimino]bis[2-4,6-trimethylbenzenesulfonicacid], di Na salt; Acid blue 80 |
| CA-Reg. No.: | 4474-24-2 |
| % Inhib. | 0 @ 1 0 ppm |
| Source: | Aldrich |
| Compound: | 7-β-D-Glucopyranosyl-9,10-dihydro-3,5,6,8-tetra-hydroxy-1-methyl-9,10-dioxo-2-anthracene carboxylic acid; Carminic acid |
| CA Reg. No.: | 1260-17-9 |
| % Inhib. | 0 @ <10 ppm |
| Source: | Aldrich |
| Compound: | 1-Amino-4[[3-[[4-chloro-6-[(3-sulfophenyl)amino]-1,3,5-triazin-2-yl]amino]-4-sulfophenyl]amino]-9,10-dihydro-9,10-dioxo-2-anthracenesulfonic acid; Reactive blue 5 |
| CA Reg. No.: | 16823-51-1 |
| % Inhib. | 0 @ 10 ppm |
| source: | Sigma |
| Compound: | N-(4-Amino-9,10-dihydro-9,10-dioxo-1-anthracenyl)-benzamide; 1-Amino-4-benzamidoanthraquinone |
| CA Reg. No.: | 81-46-9 |
| % Inhib. | 0 @ <10 ppm in 2.7% ETOH |
| Source: | Aldrich |
| Compound: | 1-Amino-4-(methylamino)anthraquinone |
| CA Reg. No.: | 1220-94-6 |
| % Inhib. | 0 @ <10 ppm in 2.7% ETOH |
| Source: | Pfaltz & Bauer |
| Compound: | 5-hydroxy-1,4-bis[(4-methylphenyl)amino]-9,10-anthracenedione; Sudan green |
| CA Reg. No.: | 4392-68-1 |
| % Inhib. | 0 @ <10 ppm in 2.7% ETOH |
| Source: | Pfaltz & Bauer |
| Compound: | 1-Bromo-4-(methylamino)anthraquinone |
| CA Reg. No.: | 128-93-8 |
| % Inhib. | 0 @ <10 ppm in 2.7% ETOH |
| Source: | Kodak |
| Compound: | 1,4-Diamino-2-methoxyanthraquinone; Disperse red 11 |
| CA Reg. No.: | 2872-48-2 |
| % Inhib. | 0 @ <10 ppm in 2.7%. ETOH |
| Source: | Sigma |
| Compound: | Indanthrene black (suspension or liquid); C.I. Vat green 9 |
| CA Reg. No.: | 6369-65-9 |
| % Inhib. | −6.5% @ <10 ppm/8% ETOH |
| source: | Pfaltz & Bauer |
| Compound: | N,N'-(9,10-Dihydro-9,10-dioxo-1,5-anthracenediyl)-bisbenzamide; 1,5-Dibenzamidoanthraquinone |

TABLE II-continued

| | |
|---|---|
| CA Reg. No.: | 82-18-8 |
| % Inhib. | 0 @ <10 ppm in 2.7% ETOH |
| Source: | K & K |
| Compound: | Alizarin blue black BC |
| CA Reg. No.: | None |
| % Inhib. | 1.9% @ <10 ppm in 2.7% ETOH |
| Source: | K & K |
| Compound: | 9,10-Dihydro-3,4,6-trihydroxy-9,10-dioxo-2-anthracenesulfonic acid; Alizarin rubinol |
| CA Reg. No.: | 83631-51-0 |
| % Inhib. | 0 @ <10 ppm in 2.7% ETOH |
| Source: | K & K |
| Compound: | 9,10-Dihydro-1,3,4,5,7,8-hexahydroxy-9,10-dioxo-2,6-anthracenedisulfonic acid; Acid alizarin blue BB |
| CA Reg. No.: | 83631-52-1 |
| % Inhib. | 0 @ <10 ppm in 2.7% ETOH |
| Source: | K & K |
| Compound: | N,N'-[Iminobis(9,10-dihydro-9,10-dioxo-5,1-anthracenediyl)]bisbenzamide; 4,5'-Dibenzamido-1,1'-dianthrimide |
| CA Reg. No.: | 129-28-2 |
| % Inhib. | 0 @ <10 ppm in 2.7% ETOH |
| Source: | Aldrich |
| Compound: | 1,4,4a,9a-Tetrahydroanthraquinone |
| CA Reg. No.: | 56136-14-2 |
| % Inhib. | 0-7% @ 10 ppm in 2.7% ETOH |
| Source: | Aldrich |

EXAMPLE 3

Inhibition of sulfide formation by 1-amino-anthraquinone

These determinations were carried out in the AutoAnalyzer ® as described in Example 1. The resulting data is shown in Table III.

TABLE III

| Compound | % inhibition of sulfide formation |
|---|---|
| Chlorhexidine | 88.7 |
| 1-amino-anthraquinone biguanide | 83 |
| 1-amino anthraquinone | 72 |

The data show that the 1-amino-anthraquinone biguanide which was derived from a chlorhexidine derivative and 1 amino-anthraquinone, as well as 1-amino-anthraquinone itself, inhibited sulfide formation by Desulfovibrio desulfuricans G100A.

EXAMPLE 4

Effect of 1,8-dihydroxyanthraquinone on growth of D. desulfuricans Gf100A

Four 10 ml culture tubes of BTZ-3 medium as defined in Example 1 supplemented with sodium lactate (40 mM) and sodium sulfate (30 mM) and 0.5 ml of reducing agent were inoculated with 100 ul of a fully grown suspension of D. desulfuricans G100A. The culture was allowed to grow and the optical density at 660 nm was monitored until the cells entered into exponential growth (approx. 12-15 h, O.D. 660=0.1-0.2). At this time 100 ul of a 300 ppm solution of 1,8 dihydroxyanthraquinone, 1-chloranthraquinone or 3-chloro-2-anthraquinone carboxylic acid, respectively, was added to one of the tubes. The ethanol:water (80:20) solvent (100 μl) was added to the fourth tube to serve as an uninhibited control. The resulting growth after the addition of the preferred inhibitors in comparison to the untreated control is shown in Table IV.

TABLE IV

| | Addition to the Bacterial Culture* | | | |
|---|---|---|---|---|
| Hours of Growth | Solvent | 1,8-dihydroxy-anthraquinone | 1-chloro-anthra-quinone | 3-chloro-2-anthra-quinone carboxylic acid |
| 0 | .01 | .01 | .01 | .01 |
| 10 | .07 | .12 | .11 | .10 |
| 12# | .11 | .20 | .12 | .16 |
| 14 | .14 | .19 | .12 | .21 |
| 18 | .25 | .16 | .27 | .36 |
| 20 | .31 | .16 | .32 | .38 |
| 24 | .65 | .16 | .32 | .36 |
| 29 | 1.0 | .18 | .30 | .37 |
| 34 | 1.2 | .18 | .32 | .37 |
| 62 | 1.2 | .30 | .26 | .34 |
| 92 | 1.2 | .28 | .23 | .25 |

*optical density reading at 660 nm
3 ppm inhibitor added at 12 hours

This example clearly shows that the addition of each of the three compounds to a final concentration of 3 ppm causes virtually complete cessation of growth of D. desulfuricans G100A for at least 80 hours.

EXAMPLES 5-10

Effect of 1,8-dihydroxyanthraquinone on different species of sulfate-reducing bacteria Different species of sulfate-reducer were grown as described in Example 1 and then 250 μl of the grown suspension was inoculated into BTZ-3 medium containing reducing agent (1.0 ml/10 ml culture) and 1,8-dihydroxyanthraquinone at 3 ppm. Growth was monitored as optical density at 660 nm for 40 hours. The resulting data is shown in Table V.

TABLE V

| Example | Desulfovibrio sp. | Control* Optical Density @ 660 nm | Treated** Optical Density @ 660 nm |
|---|---|---|---|
| 5 | D. multispirans | >1.5 | .28 |
| 6 | D. desulfuricans G100A | >1.5 | .20 |
| 7 | D. desulfuricans Norway | .30 | .09 |
| 8 | D. salexigens | >1.5 | .06 |
| 9 | D. desulfuricans #ATCC 27774 | .45 | .08 |
| 10 | D. vulgaris | .20 | .05 |

*no 1,8-dihydroxyanthraquinone present
**1,8-dihydroxyanthraquinone present

EXAMPLE 11

Effect of 1,8-dihydroxyanthraquinone on Thiobacillus denitrificans

Thiobacillus denitrificans was grown on BTZ-3 medium as defined in Example 1 (supplemented with reducing agent) and with 30 mM sodium nitrate plus 30 mM sodium thiosulfate. Cultures were anaerobic under a nitrogen atmosphere. Thus growth conditions mimicked those for the sulfate-reducing bacteria as closely as possible. The 1,8-dihydroxyanthraquinone was added to the cultures at the indicated time and the growth monitored by observing the optical density at 660 nm. The results are shown below in Table VI.

TABLE VI

| Hours of Growth | Optical Density# Control | Optical Density# +3 ppm 1,8-dihydroxyanthraquinone |
|---|---|---|
| 0 | .02 | .0 |
| 12 | .06 | .06 |
| 15 | .08 | .08 |
| 19* | .09 | .09 |

TABLE VI-continued

| Hours of Growth | Optical Density# Control | Optical Density# +3 ppm 1,8-dihydroxyanthraquinone |
|---|---|---|
| 34 | .22 | .22 |
| 36 | .29 | .25 |
| 38 | .32 | .27 |
| 43 | .40 | .32 |
| 55 | 1.5 | 1.5 |

*Time of addition of 3 ppm of anthraquinone
Optical Density @ 660 nm

Significantly, the inhibitor had no effect on the growth of *T. denitrificans*. This organism was chosen because its central metabolism involves sulfur compounds as is also the case with sulfate reducers. However, the Thiobacilli carry out the oxidation of sulfide rather than the reduction of sulfate, i.e., the reverse reaction of the sulfate reducers.

EXAMPLE 12

Effect of 1,8-dihydroxyanthraquinone on *Escherichia coli*

Another non-sulfate reducing organism, *Escherichia coli* strain MC106 was grown under aerobic conditions on BTZ-3 with 30 mM sodium succinate as sole carbon and electron source with oxygen as electron acceptor or under anaerobic conditions with hydrogen (80% as electron donor) and carbon dioxide (20%) as gas phase and sodium fumarate (30 mM) as electron acceptor. Both media contained 0.2% yeast extract. The resulting data are shown in Table VII.

TABLE VII

| | Optical Density @ 660 nm | |
|---|---|---|
| Hours | Control | +5 ppm AO* |
| Aerobic growth with succinate | | |
| 0 | 0.01 | 0.01 |
| 5.5 | 0.17 | 0.24 |
| 6.5 | 0.37 | 0.39 |
| 7.5 | 0.38 | 0.40 |
| 24 | 1.50 | 1.50 |
| Anaerobic growth under hydrogen/carbon dioxide | | |
| 0 | 0.0 | 0.01 |
| 3.5 | 0.30 | 0.29 |
| 4.5 | 0.45 | 0.62 |
| 5.5 | 0.61 | 0.79 |
| 6.0 | 0.75 | 0.87 |

*1,8-dihydroxyanthraquinone

Aerobic growth with succinate refers to growth on succinate as a carbon and electron source and oxygen as an electron acceptor. Anaerobic growth under hydrogen/carbon dioxide refers to growth with hydrogen as an electron donor and fumarate as an electron acceptor. Hydrogen consumption was observed in these cultures indicating that hydrogen was in fact used as an electron donor.

The data show virtually no inhibition by 1,8-dihydroxy-anthraquinone on the aerobic or anaerobic growth of *E. coli*.

EXAMPLE 13

Effect on 1,8-dihydroxyanthraquinone on *D. desulfurican*

*D. desulfuricans* strain G100A was grown using pyruvate fermentation in the absence of sulfate. The resulting data are shown in Table VIII.

TABLE VIII

| Hours of Growth | Optical Density# Control | Optical Density# +3 ppm Anthraquinone |
|---|---|---|
| 0 | .11 | .1 |
| 2 | .12 | .12 |
| 3.5 | .14 | .14 |
| 6.5* | .15 | .16 |
| 8.5 | .18 | .16 |
| 10.7 | .19 | .17 |
| 25 | .26 | .22 |
| 32 | .37 | .34 |
| 45 | .46 | .45 |

*Time of addition of 3 ppm 1,8-dihydroxyanthraquinone
Optical Density @660 nm

The anthraquinone did not affect fermentative growth of *D. desulfuricans* G100A. This shows that the inhibitory effects of anthraquinones are specific for sulfate reduction. Pyruvate fermentation does not involve the same enzyme systems utilized by the sulfate reduction pathway.

EXAMPLE 14

Effect of 1,8-dihydroxyanthraquinone on sulfide production by crude enrichments from various naturally-occuring environments All samples were grown on standard BTZ-3 medium (as defined in Example 1) under hydrogen (80%) carbon dioxide (20%) with 10 mM acetate and 0.1% yeast extract. Mud samples were inoculated into this medium and allowed to grow for 24 h to enrich for sulfate reducing bacteria. A 1 ml aliquot of this enrichment was transferred to fresh medium and the sulfide evolved was measured over a three day period. Sulfide was assayed as described by Siegal, Anal. Biochem. 11: 126–132, 1965, herein incorporated by reference. The resulting data are shown in Table IX.

TABLE IX

| Sample Source | Control umol sulfide/day | Treated umol sulfide/day* |
|---|---|---|
| VS-A | 49.0 | −1.0 |
| VS-AN | 12.0 | −4.0 |
| VS-AN2 | 116.0 | 0.0 |
| VF-A | 24.0 | −2.0 |
| VF-A2 | 64.0 | −11.0 |
| VF-AN | 67.0 | 2.8 |
| WCC-A1 | 411.0 | 67.0 |
| WCC-A2 | 388.0 | 49.0 |
| WCC-AN1 | 345.0 | 80.0 |
| WCC-AN2 | 288.0 | 37.0 |
| WADS | 106.7 | 71.0 |
| SM-Lewes | 6.4 | 4.5 |

VS = Valley Stream State Park, Long Island, NY
VF = Valley Garden Park, DE
WCC = White Clay Creek Preserve, PA
WADS = Wilmington anaerobic digestor, DE
SM-Lewes = Lewes saltmarsh, DE
A = aerobic samples
AN = anaerobic samples
*Cultures contain 5 ppm 1,8-dihydroxyanthraquinone The data shows that the majority of enrichments from natural sources were inhibited by the 1,8-dihydroxyanthraquinone. The cultures derived from the Wilmington anaerobic digestor or the Lewes saltmarsh were the least affected while the freshwater pond sediments showed the greatest inhibition.

EXAMPLE 15

Effect of Anthraquinones on the Respiration Rate of *D. desulfuricans* #ATCC27774

The respiration rate (rate of hydrogen gas utlized) by *D. desulfuricans* #ATCC27774 was measured with sulfate as the electron acceptor and hydrogen as the sole electron donor in the presence of each of three anthraquinones. The purpose was to show that respiration, an energy-yielding cellular reaction pathway, is sensitive to the anthraquinones, when sulfate is the electron acceptor used. Reaction mixtures had the following composition and the reactions were carried out in a Gilson respirometer flask using standard manometric techniques.

200 ul of bacterial suspension (40 mg/ml protein of bacteria)
100 ul of 1 M phosphate buffer of pH 7
250 ul of 100 mM electron acceptor anthraquinone:
2 ul of 300 ppm soln (0.6 ppm final conc.)
10 ul of 300 ppm (3 ppm)
20 ul of 300 ppm (6 ppm)
DI water to 1.0 ml The bacteria, water, buffer and inhibitor were incubated for 30 minutes under a 100% hydrogen atmosphere and then the electron acceptor was tipped into the main compartment and the reaction started. Gas uptake was measured over a period of 240 min and rates of gas uptake determined. The results are summarized below in Table X as percent of the rates of hydrogen gas uptake relative to those from mixtures incubated in the absence of anthraquinone.

TABLE X

| Concencration (ppm) | Gas Uptake (as percent of control) | | |
|---|---|---|---|
| | 1-Chloro-anthraquinone | 1,8-Dihydroxy-anthraquinone | 3-Chloro-2-anthraquinonecarboxylic acid |
| 0 | 100 | 100 | 100 |
| .6 | 74 | 66 | 79 |
| 1.5 | 50 | 45 | 55 |
| 3 | 38 | 30 | 41 |

This experiment shows that at 3 ppm the three anthraquinone inhibitors gave a 59-70% inhbition of control respiration rates. This both supports the result of Example 4 showing that 3 ppm inhibits bacterial growth and further demonstrates that the sulfate reduction process is directly affected.

EXAMPLES 16-19

Effect of Anthraquinones on Respiration Rates of *D. desulfuricans* #ATCC27774

The following experiments show the effect of the 1,8-dihydroxy-anthraquinone on the rate of hydrogen utilization by bacteria in the presence of different electron acceptors. The method used was identical to that of Example 10, and the results are summarized in Tables XI, XII, XIII and XIV.

EXAMPLE 16

TABLE XI

| Sulfite as electron acceptor (no sulfate present) with and without 3 ppm anthraquinone | | |
|---|---|---|
| | Hydrogen, µl | |
| Minutes | Control | +3 ppm 1,8-dihydroxy-anthraquinone |
| 0 | 0 | 0 |
| 6 | 7 | 7 |
| 16 | 26 | 25 |
| 26 | 45 | 43 |
| 59 | 139 | 141 |
| 71 | 179 | 183 |

EXAMPLE 17

TABLE XII

| Fumarate as electron acceptor (no sulfate present) with and without 3 ppm anthraquinone | | |
|---|---|---|
| | Hydrogen, µl | |
| Minutes | Control | +3 ppm 1,8-dihydroxy-anthraquinone |
| 0 | 0 | 0 |
| 10 | 9 | 8 |
| 25 | 23 | 25 |
| 40 | 47 | 48 |
| 55 | 70 | 74 |
| 70 | 95 | 101 |

EXAMPLE 18

TABLE XIII

| Thiosulfate as electron acceptor (no sulfate present) with and without 3 ppm anthraquinone | | |
|---|---|---|
| | Hydrogen, µl | |
| Minutes | Control | +6 ppm 1,8-dihydroxy-anthraquinone |
| 0 | 0 | 0 |
| 11 | 38 | 33 |
| 21 | 90 | 73 |
| 31 | 144 | 118 |
| 41 | 204 | 176 |

EXAMPLE 19

TABLE XIV

| Sulfate as electron acceptor with and without 3 ppm anthraquinone | | |
|---|---|---|
| | Hydrogen, µl | |
| Minutes | Control | +3 ppm 1,8-dihydroxy-anthraquinone |
| 0 | 0 | 0 |
| 10 | 15 | 3 |
| 25 | 44 | 14 |
| 40 | 76 | 21 |
| 55 | 107 | 28 |
| 70 | 152 | 38 |
| 85 | 208 | 45 |
| 100 | 266 | 56 |
| 115 | 336 | 74 |

Examples 11-14 show that the sulfate-reduction pathway is specifically affected. Alternate electron acceptors (i.e, sulfite, thiosulfate and fumarate, Examples 16-18) show comparable respiration rates with and without anthraquinone hence the anthraquinones exhibit specificity for sulfate reduction.

EXAMPLE 20

Effect of reduced anthraquinones on growth of G100A and BTZ-3 +30 mM sodium lactate+30 mM sodium sulfate Three anthraquinones, 1,8-dihydroxy-, 1-chloro-, and 3-chloro-2-carboxy- were prepared as 1 ml of 1000 ppm solutions in acetone for the first two compounds or water for the third. These solutions were then treated with 1 mg of the strong reducing agent, sodium dithionite. 50 ul of each solution (for a final culture concentration of 5 ppm) was used immediately to treat growing cultures of *D. desulfuricans* G100A in BTZ-3 medium as defined in Example 1. The compounds were added to the 10 ml cultures at 15 h of growth.

TABLE XV

| | Optical Density @ 660 nm | | | |
|---|---|---|---|---|
| Hours | 1,8 diOH | 1-Chloro | 3-Chloro-2-COOH | Control |
| 0 | 0.02 | 0.02 | 0.02 | 0.02 |
| 2 | 0.02 | 0.02 | 0.02 | 0.02 |
| 12 | 0.10 | 0.08 | 0.07 | 0.08 |
| 15 | 0.2 | 0.15 | 0.1 | 0.18 |
| 17 | 0.24 | 0.20 | 0.15 | 0.26 |
| 20 | 0.23 | 0.21 | 0.17 | 0.37 |
| 25 | 0.22 | 0.22 | 0.17 | 0.50 |
| 30 | 0.23 | 0.22 | 0.16 | 0.98 |
| 45 | 0.25 | 0.24 | 0.22 | 1.50 |

The data show that 5 ppm of any of the three preferred anthraquinones will inhibit the growth of *D. desulfuricans* G100A even when pre-reduced by dithionite to the reduced form.

EXAMPLE 21

Assay of sulfide inhibition by anthraquinones using resting cells of *D. gigas*

Experiments in this example were carried out using resting cells of *Desulfovibrio gigas* rather than growing cells as was the case for the autoanalyzer system employing the *Desulfovibrio desulfuricans* G100A strain. The reason for this was that the *D. gigas* strain retained respiratory activity under resting cell conditions whereas the *D. desulfuricans* G100A strain did not. Thus the experiment examined a different organism, different test system, and a different physiological state for the phenomenon of anthraquinone inhibition of sulfide production by Desulfovibrio sp. Active compounds, as determined by the autoanalyzer, were evaluated in comparison with four additional compounds not evaluated in the autoanalyzer. The date confirmed the inhibitory properties of the 1,8-dihydroxyanthraquinone, the 1-chloroanthraquinone and demonstrated the inhibitory effect of four new compounds not screened by the autoanalyzer method: the 2-bromoanthraquinone (CA Reg. No. 572-83-8), 1-fluoroanthraquinone (CA Reg. No. 569-06-2), 1-cyanoanthraquinone (CA Reg. No. 38366-32-4) and 2-trifluoromethylanthraquinone (CA Reg. No. 362-21-0).

500 ml cultures of *Desulfovibrio gigas* were grown on standard BTZ-3 medium as previously described in Example 1 with 30 mM sodium lactate, 30 mM sodium sulfate and 30 mM sodium fumarate. The culture was harvested after 24 h of growth at 31° C. by centrifugation at 8000 rpm in a GSA Sorvall rotor for 20 minutes. The cell pellet was resuspended in 30 ml of incubation assay mixture of the following composition: 50 mM HEPES buffer pH 7 buffer, 2.5 mM sodium lactate, 2.5 mM sodium sulfate. This suspension was centrifuged again at 10,000 rpm in a Sorvall SS-34 rotor for 5 minutes. The resulting cell pellet was resuspended in 5 ml of incubation assay buffer. Cell densities were generally near 10e10 cells/ml.

The samples were assayed for production in the presence of anthraquinones. 200 ul of the cell suspension was added to 1.2 ml of incubation assay mixture in a 5 ml capacity test tube. The tube was gassed with hydrogen gas for 20 minutes then the anthraquinones were added as ethanolic solutions, the tubes were then gassed with hydrogen again for 5 minutes. The reaction mixtures were then incubated for 3 hours at 31° C. The reactions were stopped by the addition of 200 ul of 1N sodium hydroxide. After 20 minutes the alkaline mixtures were centrifuged in a table top microfuge for 4 minutes at 14,000 rpm to remove cells and cell debris. The supernatant was then assayed for sulfide using the ferric chloride-DPD reagent system as described by Siegel et al., Anal. Blochem., 11:126–132, 1965, herein incorporated by reference. The results are summarized in Table XVI.

TABLE XVI

| | % Sulfide Production | | | | | |
|---|---|---|---|---|---|---|
| PPM | 1,8 diOH— | 2-Br | 1-Cl | 1-Fl | 1-CN | 2 TriF Me |
| 0 | 100 | 100 | 100 | 100 | 100 | 100 |
| 0.1 | 101 | 99 | 81 | 105 | 118 | 99 |
| 0.5 | 51 | 33 | 26 | 23 | 20 | 17 |
| 2 | 4 | 0.6 | 1.6 | 0.9 | 6.7 | 1.7 |
| 5 | 2.3 | 0.6 | 1.3 | 0.9 | 6.8 | 1.5 |

The halo-derivatives as well as the cyano and hydroxy compounds displayed inhibitory properties with 50% or more inhibition of sulfide production in the 0.1–0.5 ppm range.

What is claimed is:

1. A process for inhibiting sulfide production by sulfate-reducing bacteria comprising contacting a medium containing the sulfate-reducing bacteria with one or more of the following compounds under conditions and in an amount sufficient to inhibit sulfide production:

N-[1-(9,10-dihydro-9,10-dioxo)anthracenyl]-N'-(1-methylethyl)imidodicarbonimidic diamide hydrochloride;
1-Aminoanthraquinone;
2-Aminoanthraquinone;
1-Amino-4-hydroxyanthraquinone;
1,2-Diaminoanthraquinone;
2,6-Dihydroxyanthraquinone;
Anthraquinone-2-carboxylic acid;
1,5-Dihydroxyanthraquinone;
1,2-Dihydroxyanthraquinone;
2,2'-[(9,10-Dihydro-9,10-dioxo-1,5-anthracenediyl)-diimino]bis[5-methylbenzenesulfonic acid], di Na salt;
1,2,5,8-Tetrahydroxyanthraquinone;
4-Amino-9,10-dihydro-1,3-dihydroxy-9,10-dioxo-2-anthracenesulfonic acid, monosodium salt;
1,8-Dihydroxyanthraquinone;
2,2'-[(9,10-Dihydro-9,10-dioxo-1,4-anthracenediyl)-diimino]bis[5-methylbenzenesulfonic acid], di Na salt;
1-Amino-2,4-dibromoanthraquinone;
5-Chloro-1-anthraquinonylamine;
2-Ethylanthraquinone;
1-Hydroxyanthraquinone;
2-(Hydroxymethyl)anthraquinone;
1-Amino-4-methoxyanthraquinone;
1-Amino-6,7-dichloroanthraquinone;
Benz[a]anthracene-7,12-dione;

1,8-Dihydroxy-3-methylanthraquinone;
10-[(3-Amino-2,3,6-trideoxy-alpha-L-lyxo-hexopyranosyl)oxy]-7,8,9,10-tetrahydro-6,8,11-trihydroxy-8-(hydroxyacetyl)-1-methoxy-5,12-naphthacenedione hydrochloride;
9,10-Dihydro-4,5-dihydroxy-9,10-dioxo-2-anthracenecarboxylic acid;
(8S-cis)-8-Acetyl-10[(3-amino-2,3,6-trideoxy-alpha-L-lyxo-hexopyranosyl)oxy]-7,8,9,10-tetrahydro-6,8,11-trihydroxy-1-methoxy-5,12-naphthacenedione hydrochloride;
1,2,4-Trihydroxyanthraquinone;
1-Aminoanthraquinone diazonium salt;
2,2'-Dimethyl-[1,1'-bianthracene]-9,9',10,10'-tetrone;
3-(D-apio-beta-D-Furanosyloxy)-1,8-dihydroxy-6-methyl-9,10-anthracenedione;
2-Chloroanthraquinone;
1,5-Dichloroanthraquinone;
1,4,5,8-Tetrachloroanthraquinone;
1-Chloroanthraquinone;
1,8-Dichloroanthraquinone;
2-Bromo-3-methylathraquinone;
2-(2,2,2-Trimethylpropionamido) anthraquinone;
2,6-Bis[2-(dimethylamino)ethoxy]-9,10-anthracenedione;
2-Methyl-1-nitroanthraquinone;
1-Amino-9,10-dihydro-9,10-dioxo-2-anthracenesulfonic acid;
9,10-Dihydro-5-nitro-9,10-dioxo-1-anthracenesulfonic acid;
3-Chloro-9,10-dihydro-9,10-dioxo-2-anthracenecarboxylic acid;
50/50 Mixture by weight of 1,5-Dihydrocyanthraquinone and 1,8-Dihydroxycyanthraquinone;
Anthraquinone;
1,8-Dihydroxy-3-(hydroxymethyl)-anthraquinone;
7,16-Dichloro-6,15-dihydro-5,9,14,18-anthrazinetetrone;
1,2,3,4,5,8-Hexahydroxyanthraquinone;
2,4,5,7-Tetrabromo-1,8-dihydroxy-9,10-anthracenedione;
1,2,7-Trihydroxyanthraquinone;
1,4,5-Trihydroxy-2-methyl-9,10-anthracenedione;
1,4,5,7-Tetrahydroxy-2-methyl-9,10-anthracenedione;
1,8-Dihydroxy-3-methoxy-6-methyl-9,10-anthracenedione;
1,4,5,8-Tetrahydroxy-2-methyl-9,10-anthracenedione;
1,5,8-Trihydroxy-3-methyl-9,10-anthracenedione;
1-Hydroxy-2-[(6-O-β-D-xylopyranosyl-β-D-glycopyranosyl)oxy]-9,10-anthracenedione;
2-Phenoxy quinizarin-3,4'-disulfonic acid, di K salt;
(+,−)-1-Acetoxy-8-hydroxy-1,4,4a,9a-tetrahydroanthraquinone;
1-Amino-4-[4-[(dimethylamino)methyl]phenyl]amino-9,10-anthracenedione;
1,5-Bis(2-carboxyanilino)-9,10-anthracenedione;
1,8-Dihydroxy-9-anthranol;
1,2,10-Anthracenetriol;
1-Amino-4-bromo-2-methylanthranquinone;
1,4-Diaminoanthraquinone;
2,6-Diaminoanthraquinone;
1-Amino-4 [4-[[4-chloro-6-[2,3, or 4-sulfophenyl]amino]-1,3,5-triazin-2-yl]amino]-3-sulfophenyl]amino]-9,10-dihyro-9, 10-dioxo-2-anthracenesulfonic acid;
Anthraquinone-1,5-disulfonic acid, di Na salt hydrate;
Anthraquinone-2,6-disulfonic acid, di Na salt;
Anthraquinone-2-sulfonic acid, sodium salt monohydrate;
1,2-Bis[(4-sulfophenyl)amino]-4-hydroxyanthraquinone;
3-Aminomethylalizarin-N,N-diacetic acid;
1-Amino-4-[[3-(ethenylsulfonyl)phenyl]-9,10-dihydro-9,10-dioxo]-2-anthracene sulfonic acid, monosodium salt;
1-(Methylamino)anthraquinone;
2,2'-[(9,10-Dihydro-5,8-dihydroxy-9,10-dioxo-1,4-anthracendiyl)diimino]bis[5-methylbenzenesulfonic acid], di Na salt;
2,2'-[(9, 10-Dihydro-9,10-dioxo-1,4-anthracenediyl)diimino]bis[5-butylbenzenesulfonic acid];
1,1'-Iminobis[4-amino]9,10-anthracenedione, sulfonated;
1-Amino-9,10-dihydro-9,10-dioxo-4-(phenylamino)-2-anthracenesulfonic acid, Na salt;
4-[[4-(Acetylamino)phenyl]amino]-1-amino-9,10-dihydro-9,10-dioxo-2-anthracenesulfonic acid, Na salt;
1-Amino-9,10-dihydro-9,10-dioxo-4-[[3[[2-(sulfoxy)ethyl]sulfonyl]phenyl]amino]-2-anthracenesulfonic acid, disodium salt;
1-Amino-4-[3-[4,6-dichloro-1,3,5-triazin-2-yl)amino]-4-sulfophenyl]amino]-9,10-dihydro-9,10-dioxo-2-anthracenesulfonic acid;
1-(9,10-Dihydro-9,10-dioxo-1-anthracenyl)-1,2-hydrazinedisulfonic acid, di Na salt;
9,10-Dihydro-5,6-dihydroxy-9,10-dioxo-1-anthracenesulfonic acid;
N-(4-Chloro-9,10-dihydro-9,10-dioxo-1-anthracenyl)-benzamide;
1-Amino-4-bromo-9,10-dihydro-9,10-dioxo-2-anthracenesulfonic acid, Na salt;
1-Amino-9,10-dihydro-4[[(4-methylphenyl)sulfonyl]amino]-9,10-dioxo-2-anthracenesulfonic acid, Na salt;
9,10-Dihydro-9,10-dioxo-2,3-anthracenedicarboxylic acid;
1,1'-Iminobis(4-nitro-9,10-anthracenedione);
1-Amino-4-chloro-2-methylanthraquinone;
2,3-dimethyl-1,4-dihydroxyanthraquinone;
6-Methyl-1,3,8-trihydroxyanthraquinone;
1,4-Bis(methylamino)-anthraquinone;
N-(4-Amino-9,10-dihydro-3-methoxy-9,10-dioxo-1-anthracenyl)-4-methylbenzenesulfonamide;
[1,1'-Bianthracene]-9,9'10,10'-tetrone;
6,7-Dichloro-1,4-dihydroxyanthraquinone;
2-[[9,10-Dihydro-4-(methylamino)-9,10-dioxo-1-anthracenyl]amino]-5-methyl-benzenesulfonic acid, monosodium salt;
2,8-Diphenyl-anthra[2,1-d:6,5-d']bisthiazole-6,12-dione;
2-Methoxy-3-methyl-9,10-anthracenedione;
1,4-Bis[(1-methylethyl)amino]-9,10-anthracenedione;
1,4-Bis[(2,4,6-triethylphenyl)amino]-9,10-anthracenedione;
1-(2-Hydroxyethyl)amino-4-methylaminoanthraquinone;
1,4-Bis[(4-methylphenyl)amino]9,10-anthracenedione;
2-Amino-3-hydroxyanthraquinone;
1-(Bromothio)anthraquinone;
1,8-Bis(phenylmethoxy)-9,10-anthracenedione;
1-Amino-2-(2-aminoethylthio)-4-hydroxyanthraquinone;
1,4-Bis(pentylamino)-9,10-anthracenedione;
1-Amino-2-bromo-4-hydroxyanthraquinone;
2-Propionamidoanthraquinone;
1,4-Diamino-2,3-bis(2-phenoxyethoxy)anthraquinone;

N-(5-Chloro-9,10-dihydro-9,10-dioxo-1-anthracenyl)-benzamide;
Anthraquinone-1-arsonic Acid;
N,N'-[Iminobis(9,10-dihydro-9,10-dioxo-4,1-anthracenediyl)]-bisbenzamide;
1,4,5,8-Tetraaminoanthraquinone;
2-Methylanthraquinone;
9,10-Dihydro-9,10-dioxo-2,7-anthracenedisulfonic acid, di Na salt;
1,2,3-trihydroxyanthraquinone;
9,10-Dihydro-1,4-dihydroxy-9,10-dioxo-2-anthracenesulfonic acid;
2-Amino-3-chloroanthraquinone;
1-Anthraquinonesulfonic acid, Na salt;
2-tert-butylanthraquinone;
1,4-Dihydroxyanthraquinone;
1,5-Diamino-4,8-dihydroxyanthraquinone;
1-Hydroxy-4-[(4-methylphenyl)amino]-9,10-anthracenedione;
1,4-Dimethylanthraquinone;
1,1'-Iminobis-9,10-anthracenedione;
2-(Cyclopropylcarboxamido)anthraquinone;
1-Amino-2-methylanthraquinone;
2-[(9,10-Dihydro-4-hydroxy-9,10-dioxo-1-anthracenyl)amino]-5-methyl-benezensulfonic acid, Na salt;
2,2'-[(9,10-Dihydro-5,8-dihydroxy-9,10,dioxo-1,4-anthracenediyl)diimino]bis[5-methyl]benzenesulfonic acid;
1,4-Bis(ethylamino)-9,10-anthracenedione;
1,4-Diamino-5-nitroanthraquinone;
N-Benzyl-9,10-dihydro-9,10-dioxo-2-anthracenesulfonamide;
2-Bromoanthraquinone;
1-Fluoroanthraquinone;
1-Cyanoanthraquinone and;
2-Trifluoromethylanthraquinone.

2. The process of claim 1 for inhibiting sulfide production by sulfate-reducing bacteria, wherein the medium is contacted with a mixture of at least two of said compounds.

3. The process of claim 1 wherein the compound is 1,8-dihydroxyanthraquinone.

4. The process of claim 1 wherein the compound is 1-chloroanthraquinone or 2-chloroanthraquinone.

5. The process of claim 1 wherein the compound is 3-chloro-9,10-dihydro-9,10-dioxo-2-anthracenecarboxylic acid.

6. The process of claim 1 wherein the compound is 2-bromoanthraquinone.

7. The process of claim 1 wherein the compound is 1-fluoroanthraquinone.

8. The process of claim 1 wherein the compound is 1-cyanoanthraquinone.

9. The process of claim 1 wherein the compound is 2-Trifluoromethylanthroquinone.

10. The process of claim 1 wherein the compound is anthraquinone.

11. The process of claim 1 wherein the sulfate-reducing bacterium is selected from the group consisting of *Desulfovibrio desulfuricans, D. salexigens, D. vulgaris, D. multispirans,* and *D. gigas.*

12. The process of claim 1 wherein the one or more compounds are dissolved or suspended in a solvent prior to contact with the medium wherein said solvent is selected from the group consisting of water, ethanol, acetone, methanol, dimethylsulfoxide, dimethylformamide, or tetrahydrofuran, and other water-miscible solvents.

13. The process of claim 1 wherein the one or more compounds are contacted with the medium at a concentration of at least about 0.1 ppm.

14. The process of claim 1 further comprising addition of a reducing agent to the medium containing the sulfate-reducing bacteria to enhance inhibition.

15. The process of claim 14 wherein the reducing agent is sodium sulfide and is present in the medium at a concentration of from about 2 to about 4 mM.

16. The process of claim 1 wherein said medium is sewage.

17. The process of claim 1 wherein sulfate production by the sulfate-reducing bacteria is reduced by the contacting of the medium with the one or more of said compounds.

18. A process for inhibiting sulfide production by sulfate-reducing bacteria, the process comprising contacting an anaerobic medium containing the bacteria with an anthraquinone, the anthraquinone selected from the group consisting of 9,10-anthraquinone, 1,8-dihydroanthraquinone, 1-chloroanthraquinone, 2-chloroanthraquinone, 2-bromoanthraquinone, and 1-fluoroanthraquinone, so that the final concentration of anthraquinone is at least 0.1 ppm.

19. The process of claim 18 wherein the anthraquinone is 9,10-anthraquinone.

20. The process of claim 19 wherein said medium is sewage.

21. The process of claim 19 in which the species of the sulfate-reducing bacteria is selected from the group consisting of *Desulfovibrio desulfuricans, D. salexigens, D. vulgaris, D. multispirans,* and *D. gigas.*

22. An aqueous anaerobic medium comprising sulfate-reducing bacteria and at least 0.1 ppm of an anthraquinone, the anthraquinone selected from the group consisting of 9,10-anthraquinone, 1,8-dihydroanthraquinone, 1-chloroanthraquinone, 2-chloroanthraquinone, 2-bromoanthraquinone, and 1-fluoroanthraquinone.

23. The medium of claim 22 in which the species of the sulfate-reducing bacteria is selected from the group consisting of *Desulfovibrio desulfuricans, D. salexigens, D. vulgaris, D. multispirans,* and *D. gigas.*

24. The medium of claim 22 in which the anthraquinone is 9,10-anthraquinone.

25. The medium of claim 24 in which the species of the sulfate-reducing bacteria is selected from the group consisting of *Desulfovibrio desulfuricans, D. Salexigens, D. vulgaris, D. multispirans,* and *D. gigas.*

* * * * *